(12) United States Patent
Takesue et al.

(10) Patent No.: US 9,194,818 B2
(45) Date of Patent: Nov. 24, 2015

(54) DISTANCE MEASUREMENT SYSTEM AND OPTICAL RESOLUTION IMPROVEMENT APPARATUS

(71) Applicant: ASTRODESIGN, Inc., Tokyo (JP)

(72) Inventors: Toshiharu Takesue, Tokyo (JP); Shigeto Takeda, Tokyo (JP); Shigeaki Suzuki, Tokyo (JP)

(73) Assignee: ASTRODESIGN, INC., Tokyo (JP)

( * ) Notice: Subject to any disclaimer, the term of this patent is extended or adjusted under 35 U.S.C. 154(b) by 196 days.

(21) Appl. No.: 13/864,668

(22) Filed: Apr. 17, 2013

(65) Prior Publication Data

US 2013/0280798 A1  Oct. 24, 2013

(30) Foreign Application Priority Data

Apr. 20, 2012  (JP) ................................. 2012-096551
May 14, 2012  (JP) ................................. 2012-110562

(51) Int. Cl.
*G01B 9/02* (2006.01)
*G01N 22/00* (2006.01)
(Continued)

(52) U.S. Cl.
CPC .............. *G01N 22/00* (2013.01); *G01S 7/4814* (2013.01); *G01S 17/36* (2013.01)

(58) Field of Classification Search
CPC .... G01B 11/14; G01B 11/026; G01B 11/028; G01B 9/02019; G01B 9/02002; G01S 17/66; G01S 17/08
USPC ......................................... 356/486, 487, 489
See application file for complete search history.

(56) References Cited

U.S. PATENT DOCUMENTS

| 4,417,813 A | * | 11/1983 | Bartholomew | ............... 356/489 |
| 5,481,360 A | | 1/1996 | Fujita | |
| 5,751,243 A | | 5/1998 | Turpin | |

(Continued)

FOREIGN PATENT DOCUMENTS

| EP | 0539757 | 5/1993 |
| GB | 2142427 | 1/1985 |

(Continued)

OTHER PUBLICATIONS

Extended European Search Report dated Oct. 22, 2013 issued in counterpart application No. 13164457.7.

(Continued)

*Primary Examiner* — Jonathan Hansen
(74) *Attorney, Agent, or Firm* — Kratz, Quintos & Hanson, LLP

(57) ABSTRACT

A distance measurement system includes: an irradiating means for irradiating two coherent electromagnetic waves having frequencies different from each other to an object under measurement in a partially displacing manner while having a same area; an electromagnetic wave detecting means for detecting electromagnetic waves from at least two or more areas on the object under measurement with a boundary line being interposed therebetween to extend in a direction substantially perpendicular to the displacement direction; a signal generating means for generating a difference signal or a summation signal of respective outputs of the electromagnetic waves detected in the electromagnetic wave detecting means at symmetrical positions with respect to the boundary line; and a measuring means for obtaining a phase difference or intensity difference of the difference signal or summation signal to obtain measurement values.

20 Claims, 16 Drawing Sheets

(51) Int. Cl.
*G01S 17/36* (2006.01)
*G01S 7/481* (2006.01)

(56) References Cited

U.S. PATENT DOCUMENTS

2007/0087445 A1 4/2007 Tearney et al.
2007/0091316 A1* 4/2007 Lal et al. .................... 356/486
2011/0176565 A1* 7/2011 Hutchin ........................ 372/27

FOREIGN PATENT DOCUMENTS

JP   S59-214706   12/1984
WO   02/103287    12/2002

OTHER PUBLICATIONS

D.K. Hamilton, et al.; "Differential phase contrast in scanning optical microscopy;" Journal of Microscopy; vol. 133; Part 1; Jan. 1984; pp. 27-39 (13 Sheets).

* cited by examiner

DISTANCE MEASUREMENT SYSTEM AND OPTICAL RESOLUTION IMPROVEMENT APPARATUS

BACKGROUND OF THE INVENTION

1. Field of the Invention

The present invention relates to a distance measurement system accurately measuring a distance to an object under measurement with electromagnetic waves and an optical resolution improvement apparatus realizing, with quite high resolutions, measurement or observation of the profile of a surface condition or the surface condition of a cell, or the like by irradiation of laser lights, and is preferable for improving the resolution of an optical apparatus such as a microscope.

2. Description of the Related Art

With a conventional optical microscope, it has not been possible to observe or measure an object under measurement at or below a diffraction limit. As a substitute for this, a probe microscope (STM, AFM, NFOS, or the like), a scanning electron microscope, and so on have been developed and used in many fields. The scanning electron microscope uses a very narrow beam as a scanning electron probe, and thus has a high resolution and a significantly large focal depth as compared to the optical microscope. However, for measuring an object under measurement with low electric conductivity such as a cell, it is necessary to coat platinum palladium or gold with good electric conductivity on a sample as the object under measurement. Accordingly, this often accompanies damage to a cell itself, and of course it has not been possible to observe and measure a live cell.

Further, the probe microscope is to measure the distance to the object under measurement by making a probe, which is disposed close to the object under measurement, further close to the object under measurement, and utilizing atomic force, tunnel current, light near field or the like. However, it is difficult to move the probe at high speed, handling is difficult because the distance to the object under measurement is quite close, and moreover a long time is needed for obtaining two-dimensional information.

On the other hand, it is also conceivable to apply a system which irradiates an electromagnetic wave like a radar does, detects an electromagnetic wave from an object under measurement, and measures the distance to the object under measurement basically by a time difference between the time of transmission and the time of reception. However, in such a system, various signal processing algorithms are required and hence it is complicated, and also the size of the detectable object under measurement is limited.

On the other hand, for measuring a distance accurately or for measuring or observing a minute object accurately, heterodyne interference methods are well known. Here, an optical heterodyne method using lights will be described, but it is also performed with the similar idea for other electromagnetic waves. This optical heterodyne method makes two laser lights with different frequencies interfere with each other to create a beat signal of the frequency difference, and detects a phase change of this beat signal with a resolution of about 1/500 of a wavelength. That is, with this optical heterodyne method, it is possible to measure the distance to an object under measurement while measuring a change in height direction of a surface, or to measure or observe an object under measurement itself.

Then, Japanese Patent Application Laid-open No. S59-214706 of Patent Document 1 below discloses a method to adjacently generate two beams composed of different frequencies by using an acoustic optical device, detect a phase change between these two beams, and obtain a surface profile by increasing the phase change cumulatively. However, this Patent Document 1 is to make two beams be close and slightly larger than a beam profile, detect an average phase difference in two beam profiles by heterodyne wave detection, and sequentially integrate the phase difference, so as to obtain concave and convex information.

Therefore, according to this Patent Document 1, it is possible to measure concave and convex information of an object under measurement which is assumed to be flat such as a semiconductor wafer, but it is not possible to extract information inside the beam profile. Accordingly, it is not possible to increase the resolution inside the beam profile, which is in a plane.

On the other hand, a method called DPC (Differential Phase Contrast) method has been conventionally known. This is a technique applied first to an electron microscope by Dekkers and de Lang, and is thereafter expanded to an optical microscope by Sheppard and Wilson and others. This DPC method obtains a differential signal of results of interference between a zero order diffracted light and a first order diffracted light detected by detectors, which are in a far field with respect to electromagnetic waves irradiated to a sample and disposed symmetrically with respect to an irradiation axis of the electromagnetic waves, to thereby obtain profile information of the sample. However, when a spatial frequency increases, this DPC method is not able to make these zero order diffracted light and first order diffracted light interfere, and as a result of that the spatial frequency cannot be reproduced, the measurement can no longer be performed in some cases.

That is, including general apparatuses and the like using electromagnetic waves, conventional imaging-type microscopes using electromagnetic waves cannot exceed a resolution which is the limit of the Abbe's theory. This limit is a result of a diffraction phenomenon which a wave has, and has been assumed as a theological limit that cannot be exceeded. Therefore, it has been difficult to overcome the substantial limit by wavelengths used in not only the optical microscopes but also the electron microscopes.

Patent Document 1: Japanese Patent Application Laid-open No. 559-214706 (JP59214706(A))

As described above, in a conventional distance measurement apparatus using the heterodyne detection, it has not been possible to measure a distance with a resolution equal to or smaller than the wavelength of an electromagnetic wave to be given. Therefore, even when the irradiation area of the electromagnetic wave is decreased to be equal to or smaller than a wavelength, it has only been possible to calculate an average distance of an area to the extent equal to or larger than the wavelength.

Similarly, in a conventional optical detector using the heterodyne detection, a near-flat object such as a semiconductor wafer is a main target of measurement. Accordingly, to increase the resolution in a plane, it has been inevitable to use the near field of the electronic microscope, AFM (atomic force microscope), or the like.

However, regarding the electronic microscope, processing of a living organism, cell, or the like in particular is necessary, and thus live observation or measurement of a refractive-index distribution is not possible. On the other hand, the AFM has insufficient processing speed and hence is unable to see a change of state in real time. Thus, it is not suitable for observation of a living organism or cell, and meanwhile the probe needs to be close to the object under measurement, which causes poor usability.

Here, the OTF characteristics of an objective lens in a conventional microscope using an imaging optical system will be described below.

In the conventional microscope using an imaging optical system, the component of a first order diffracted light and the component of a zero order diffracted light of the spatial frequency of a target object, which is captured with the objective lens, interfere with each other to form an image. Accordingly, when the first order diffracted light is not incident on the aperture of the lens, the spatial frequency thereof would not be reproduced. On the other hand, the angle of diffraction of the first order diffracted light increases gradually as it varies from a low frequency to a high frequency, and hence the amount of the first order diffracted light inputted to the lens decreases progressively. As a result, the frequency whose first order diffracted light is not inputted is cut off, and the degree of modulation thereof gradually decreases in the course of variation from the low frequency to the high frequency.

The OTF characteristics of the objective lens are as described above. Therefore, in the imaging system, the first order diffracted light to be inputted to the objective lens is limited itself, and thus the resolution itself is has a limit in relation with the spatial frequency of the target object to be reproduced.

The above qualitative explanation is quantified and described in detail below.

As in FIG. 16, it is assumed that a parallel luminous flux is incident on an objective lens 31 having an aperture diameter a and a focal length f. Note that in FIG. 16, an irradiation optical axis is represented by an optical axis L0, and a tilted optical axis tilted by an angle Θ with respect to this optical axis L0 is represented by an optical axis L1. A microscope using normal imaging is a transmission type in which the luminous flux transmits a sample S as in FIG. 16, but it may be considered as a reflection type in which the luminous flux is returned by the sample S. Further, to make the equations simple, it is handled as a one-dimensional aperture.

Further, for simplicity, the sample S is assumed to be in the form of a sine wave with a height h and a pitch d. Specifically, an optical phase θ is represented by the following equation.

$$\theta = 2\pi(h/\lambda)\sin(2\pi x/d) \quad \text{Equation (1)}$$

The amplitude E of a light deflected from the sample S is given as a convolution of Fourier transform of Equation (1) and the aperture of the lens on a plane separated by the focal length f, and hence is represented as follows. However, the Bessel function which is Fourier transform of the phase of Equation (1) takes up to the positive and negative first order.

$$E = \int \left( J_0\left(2\pi\frac{h}{\lambda}\right)\delta(X) + \right.$$
$$J_1\left(2\pi\frac{h}{\lambda}\right)\left(\delta\left(X - \frac{\lambda f}{d}\right) - \delta\left(X + \frac{\lambda f}{d}\right)\right)\right) rect\left(\frac{x-X}{2a}\right) dx$$
$$= J_0\left(2\pi\frac{h}{\lambda}\right) rect\left(\frac{x}{2a}\right) + J_1\left(2\pi\frac{h}{\lambda}\right)$$
$$\left( rect\left(\frac{x - \frac{\lambda f}{d}}{2a}\right) - rect\left(\frac{x + \frac{\lambda f}{d}}{2a}\right) \right)$$

Equation (2)

Here, the Fourier transform of Equation (2) contributes to imaging.

Therefore, intensity I is as following Equation (3)

$$I = \left(J_0\left(2\pi\frac{h}{\lambda}\right) * a * \text{sinc}(ka)\right)^2 +$$
$$2 * \left(J_1\left(2\pi\frac{h}{\lambda}\right) * \left(a - \frac{\lambda f}{2d}\right) * \text{sinc}\left(k\left(a - \frac{\lambda f}{2d}\right)\right)\right)^2 *$$
$$\left(4\sin^2\left(2\pi\frac{x}{d}\right)\right)$$

Equation (3)

What this equation means is that information of a pitch smaller than d=λf/2a=0.5λ/NA is dropped. This matches the beam diameter of a rectangular opening (the first dark ring diameter w of sin c(ka)=0 satisfies ka=π, and thus w=0.5×/NA). Further, this means that even when d>0.5λ/NA, the degree of modulation decreases as d becomes smaller. When the relation of this with the spatial frequency of 1/d and the degree of modulation is indicated, it is MTF.

As described above, in the ordinary imaging optical system, the limit of the spatial frequency reproduced by NA of the objective lens 31 is inevitably d=λf/2a=0.5λ/NA, and any value smaller than this would not be reproduced in any way.

SUMMARY OF THE INVENTION

The present invention is made in view of the above-described background, and a first object thereof is to provide a distance measurement system having a high resolution in a plane as well as a high resolution with respect to a height or a refractive index distribution and a high resolution of distance outside the plane.

Further, it is a second object thereof is to provide an optical resolution improvement apparatus obtaining a spatial frequency which cannot be obtained with a reproduced spatial frequency of an ordinary imaging optical system, and effectively having a high resolution.

A distance measurement system according to a first aspect of the present invention includes:

an irradiating means for irradiating two coherent electromagnetic waves having frequencies different from each other to an object under measurement in a partially displacing manner while having a same area;

an electromagnetic wave detecting means for detecting electromagnetic waves from at least two or more areas on the object under measurement with a boundary line being interposed therebetween to extend in a direction substantially perpendicular to the displacement direction;

a signal generating means for generating a difference signal or a summation signal of respective outputs of the electromagnetic waves detected in the electromagnetic wave detecting means at symmetrical positions with respect to the boundary line; and a measuring means for obtaining a phase difference or intensity difference of the difference signal or summation signal to obtain measurement values.

The operation of the distance measurement system according to the first aspect will be described below.

Two coherent electromagnetic waves having slightly different frequencies are irradiated by the irradiating means to the object under measurement separately in a partially displacing manner while most of irradiation areas are overlapped. The electromagnetic waves reflected from the object under measurement or transmitted through the object under measurement are detected by the electromagnetic wave detecting means which is a detector adapted to the irradiated electromagnetic waves. At that time, detectors divided in two or more are disposed to be capable of detecting electromagnetic waves of at least two or more areas with a boundary line being interposed therebetween to extend in a direction perpendicular to the displacement direction of the irradiated electromagnetic waves. Specifically, when these detectors are disposed at a distance which can be considered as a far field with respect to the object under measurement, these detectors detect the electromagnetic waves respectively, which become as follows.

The signal generating means generates a summation signal of all the detectors divided in two or more or a difference signal of the detectors from each other with the boundary line being interposed therebetween, allowing detection of a slight frequency difference (beat signal) based on these signals and measurement of a phase displacement from an inputted signal. In the measuring means, based on the summation signal of outputs of all the detectors, it is possible to effectively give an integral value of the area corresponding to the irradiation area of the phase difference according to the degree of separation of the areas irradiated with the two electromagnetic waves. Therefore, accompanying that the resolution of about a fraction of a wavelength is obtained according to the same principle as that for the differential interference microscope, the distance between the detectors and the object under measurement can be obtained in this resolution.

Moreover, to increase the resolution, in the measuring means, the aforementioned difference signal of the detectors from each other with the boundary line being interposed therebetween is used to effectively give an integral value of the area corresponding to the irradiation area of a differential of the phase difference according to the degree of separation of the areas irradiated with the two electromagnetic waves. In this case, as compared to the case of the summation signal, only the portion in which the phase difference has occurred contributes to the phase difference, and thus the sensitivity increases significantly.

Thus, a lateral resolution can be improved, which is comparable to the resolution according to the degree of separation of beams. This is an outstanding characteristic which cannot be found in distance measurement using the ordinary heterodyne detection. As a result, a lateral resolution much higher than a lateral resolution dominated by a wavelength can be obtained. Note that effects similar to above can be obtained also by the intensity of the beat signal.

From the above points, it is possible to obtain a distance measurement system having a high resolution with respect to a height and a refractive index distribution, capable of making the resolution of distance be about 1/500 of a wavelength, and also having a significantly high resolution in a plane. Moreover, areas where two electromagnetic waves having different frequencies are generated can be made close, and thus the path can be mostly shared. Thus, it becomes a distance measurement system which is highly resistant to external environmental changes, vibrations, and the like.

For example, two transmitting antennas generating two microwaves or radio waves having slightly different frequencies are prepared, a plurality of receiving antennas are prepared in the above-described disposition, and they are mounted on an aircraft. In this manner, the transmitting antennas almost become a point source when seen from the object under measurement. Since radio waves in the atmosphere travel the same optical path, correct distance measurement is possible even when there is shaking of the aircraft, or the like.

Further, a distance measurement system according to a second aspect of the present invention includes:
 a light source emitting a coherent light;
 a first means for modulating the light emitted from the light source into two lights which have frequencies different from each other and are irradiated separately adjacent to each other;
 a second means for one-dimensionally or two-dimensionally scanning the two lights;
 a third means for irradiating an object under measurement with the two lights which are two-dimensionally scanned;
 a fourth means for receiving at least two or more divided reflected lights or transmitted lights from the object under measurement with a boundary line being interposed therebetween in a direction substantially perpendicular to the direction in which the two lights are separated;
 a fifth means for generating a difference signal or a summation signal of respective outputs of the lights received by the fourth means in areas with the boundary line being interposed therebetween; and
 a sixth means for obtaining a phase difference or an intensity difference of the difference signal or the summation signal to obtain a measurement value.

Next, the operation of the distance measurement system according to the second aspect will be described below.

In the distance measurement system according to the second aspect, the electromagnetic waves in the distance measurement system according to the first aspect are applied to lights.

According to the present invention, a light from a light source is DSB modulated by the first means, which is an acoustic optical device, a spatial light modulator, or the like, so as to generate beams which are two lights slightly different in frequency and emission direction. By scanning these two beams by the second means, which is one-dimensional or two-dimensional scanning optical element irrelevant to a modulation frequency toward an objective lens, which is the third means, the two close beams scan the object under measurement via the objective lens.

When the object under measurement is a reflective object, a slight frequency difference (beat signal) of the beams can be detected by a photo detector, which is the fourth means disposed at a position substantially conjugate to the acoustic optical device, so as to obtain two beat signals. Further, when the object under measurement is a transmissive object, these two beat signals can be detected likewise by a photo detector disposed at a position which is in far field but not so distant from the object under measurement.

Then, when photo detectors divided in two or more with a dividing line being interposed therebetween to extend in the direction perpendicular to the separation direction of the beams are used as the photo detector, the fifth means creates a summation signal of all the photo detectors or a difference signal of the photo detectors from each other with the boundary line being interposed therebetween. Then, the sixth means detects a slight frequency difference (beat signal) based on these signals and measures a phase displacement from the inputted signal. That is, in this sixth means, based on the summation signal of outputs of all the photo detectors for example, there is effectively given an integral value of the area corresponding to the beam diameter of the phase difference according to the degree of separation of the two beams condensed by the objective lens. Accordingly, accompanying that a resolution substantially equivalent to that of the differential interference microscope is obtained, the distance between the photo detectors and the object under measurement can be obtained in this resolution.

To increase the resolution further, a difference signal of photo detectors from each other at adjacent positions in the photo detectors divided in two or more may be obtained. In this manner, there is effectively given an integral value of the area corresponding to the beam diameter of a differential of the phase difference according to the degree of separation of the two beams condensed by the objective lens. In this case, as compared to the summation signal, only the portion in which the phase difference has occurred contributes to the phase difference, and thus the sensitivity increases significantly. Therefore, a lateral resolution can be improved, which is comparable to the resolution according to the degree of separation of the beams. This is an outstanding characteristic which cannot be found in ordinary differential interference microscopes. As a result, a lateral resolution much higher than a lateral resolution dominated by a wavelength can be obtained.

To summarize, according to the present invention, it is possible to give a distance measurement system having an increased resolution with respect to a height and a refractive index distribution, high measurement accuracy of distance, and a high resolution in a plane.

Further, when the present invention is applied to a microscope, since it has a quite high in-plane resolution and moreover a height or a refractive index distribution can be measured by performing two-dimensional scanning once, three-dimensional measurement of a state change or the like of live cells, a micro-machine, or the like can be performed in real time. Accordingly, the present invention has large characteristics incomparable to conventional laser scanning type confocal microscope which obtains two-dimensional information and adds it up in a three-dimensional direction, or the like.

Moreover, when the present invention is applied to a transmission type microscope, living organisms and cells can be observed and measured alive in high resolution. Accordingly, the present invention has large characteristics which are not present in electron microscopes with which cells or the like are inactivated and then measured.

On the other hand, an optical resolution improvement apparatus according to a third aspect of the present invention includes:

a light source irradiating a light, which is irradiated convergently or irradiated in parallel, to an object under measurement;

a first light processing member located on an irradiation optical axis of the convergent irradiation or the parallel irradiation and receiving and processing a luminous flux emitted from the object under measurement;

a first photo detector having at least two divided photo detectors which receive lights of respective side portions with the irradiation optical axis being interposed therebetween within a transmitted light from the first light processing member;

a pair of second light processing members each located on a tilted optical axis having a tilt with respect to the irradiation optical axis on one of light receiving sides of the divided photo detectors of the first photo detector, and receiving and processing a luminous flux emitted from the object under measurement and making the luminous flux and a luminous flux emitted from the first light processing member interfere with each other;

a pair of second photo detectors receiving the luminous fluxes made to interfere by the pair of second light processing members; and an output difference detection unit detecting an output difference between the divided photo detectors located with the irradiation optical axis of the first photo detector being interposed therebetween and an output difference between the pair of second photo detectors.

Further, an optical resolution improvement apparatus according to a fourth aspect of the present invention includes:

a light source irradiating a light, which is irradiated convergently or irradiated in parallel, to an object under measurement;

a first optical element located on a tilted optical axis having a tilt with respect to an irradiation optical axis of the convergent irradiation or the parallel irradiation and making two luminous fluxes interfere with each other;

a plurality of first photo detectors each detecting the luminous fluxes made to interfere by the first optical element;

a second optical element located on a tilted optical axis having a tilt reverse to that of the first optical element with respect to an irradiation optical axis of the convergent irradiation or the parallel irradiation and making two luminous fluxes interfere with each other;

a plurality of second photo detectors each detecting the luminous fluxes made to interfere by the second optical element; and an output difference detection unit detecting an output value of a difference between an arbitrary light receiving output of the plurality of first photo detectors and an arbitrary light receiving output of the plurality of second photo detectors.

Next, the operations of the optical resolution improvement apparatuses according to the third and fourth aspects will be described below.

As described above, the DPC method is to obtain profile information of a sample by detecting a differential signal of the detectors from each other, which are disposed in a far field with respect to electromagnetic waves irradiated to a sample, which is an object under measurement, and disposed symmetrically with respect to an irradiation axis of electromagnetic waves.

On the other hand, the present inventors have devised a method to scan two beams having frequencies slightly different from each other and are slightly displaced in position from each other by using an acoustic optical device or the like, and heterodyne detect a differential output of a plurality of photo detectors disposed in a far field.

Then, the present invention can be said as one using a method combining the DPC method and the heterodyne method.

Incidentally, formation of an image using electromagnetic waves can be considered to be due to interference of a zero order diffracted wave and a positive and negative first order diffracted waves of a spatial frequency which the image itself has. An MTF curve of an optical system is directly related to the amount of the first order diffracted light received by an objective lens of the optical system. Therefore, a spatial frequency which has a first order diffracted light not incident on the objective lens does not contribute to imaging, and thus is cut inevitably. This maximum spatial frequency is the cut-off frequency of the optical system.

On the other hand, in the optical DPC method, a coherent light like a laser is used. Specifically, a result of interference of the first order diffracted light and the zero order diffracted light of the coherent light irradiated to a sample is reflected on photo detectors disposed in a far field symmetrically with respect to the optical axis of the coherent light, and thereby the sample which is an object under measurement is measured or observed. At that time, determination of the spatial frequency of the sample is similar to an imaging optical system.

Here, the zero order diffracted light of a light reflected by the sample or transmitted through the sample is emitted from the sample having an aperture angle of a light when irradiated, that is, the angle of divergence depending on NA of the objective lens. Similarly, the first order diffracted light changes in angle in a direction depending on the spatial frequency and is further emitted with the same angle of divergence as that of the zero order diffracted light. Therefore, the profile information of the sample is obtained in a portion where the zero order diffracted light and the positive and negative first order diffracted lights overlap on the photo detectors.

From the above, when the spatial frequency is high, the zero order diffracted light and the first order diffracted light cannot interfere with each other, and this spatial frequency is not reproduced. Accordingly, by making the zero order diffracted light and the first order diffracted light interfere with each other before guiding them to the photo detectors, significant improvement in reproduced spatial frequency is realized. Therefore, an interferometer (Fabry-perot, Mach-Zehnder, or the like) is built in a space between the sample and the photo detectors, so as to make the zero order diffracted light and the first order diffracted light interfere with each other at this position.

On the other hand, there is disposed a lens having an optical axis between the respective chief ray axes of the zero order diffracted light and the first order diffracted light. By this lens, it is conceivable that the zero order diffracted light or the first order diffracted light diffracted from the sample is converted into a parallel luminous flux, an image is reversed toward one of lights thereof by an optical element like a dove prism and further shifted in parallel by an optical element like a rhomboid prism so that the zero order diffracted light and the first order diffracted light overlap, and the zero order diffracted light and the first order diffracted light are made to is interfere with each other. By performing this through two systems, one between the first order diffracted light and the zero order diffracted light and one between the negative first order diffracted light and the zero order diffracted light, the differential signal of the two groups of photo detectors disposed in a far field has larger spatial frequency information, which substantially improves the resolution.

Further, there is disposed a lens having an optical axis between the respective chief ray axes of the zero order diffracted light and the first order diffracted light. By this lens, it is conceivable that part of the zero order diffracted light, the first order diffracted light, and part of the negative first order diffracted light are enlarged to adjust the pitch of the divided photo detectors and a formed interference pitch to be substantially the same, so as to use the photo detectors selectively.

Moreover, there is disposed a lens having an optical axis between the respective chief ray axes of the zero order diffracted light and the first order diffracted light. By converting the zero order diffracted light or the first order diffracted light diffracted from the sample into a parallel luminous flux by this lens, and guiding the zero order diffracted light and the first order diffracted light to the photo detectors by a magnifying lens system, magnified interference fringes are formed on the photo detectors. At that time, this is performed through two systems, one between the first order diffracted light and the zero order diffracted light and one between the negative first order diffracted light and the zero order diffracted light, and the photo detectors are adjusted so that when one photo detector has the maximum amount of light, the other photo detector has substantially zero amount of light.

Further, there is disposed a lens having an optical axis between the respective chief ray axes of the zero order diffracted light and the first order diffracted light. By this lens, the zero order diffracted light or the first order diffracted light emitted from the sample is converted into a parallel luminous flux, and this parallel luminous flux is condensed by the lens. Then, by a grating having an appropriate grating pitch disposed substantially in the vicinity of the focal point of the lens, the zero order diffracted light and the first order diffracted light are substantially shifted and overlapped with each other, so as to make them interfere.

Thus, the differential signal of the two groups of photo detectors disposed in a far field has larger spatial frequency information, which substantially improves the resolution. Moreover, since the present invention uses interference information of the zero order diffracted light and the first order diffracted light emitted from a sample, the influence of an irradiation optical system is small. Therefore, it is possible to increase the detected spatial frequency even when an irradiation spot is large in some degree.

The optical resolution improvement apparatus according to the present invention physically obtains an essentially high spatial frequency and hence obtains the original information which the sample has, as compared to an estimation method performing it with image processing or the like or a method of forcibly increasing the degree of modulation at a Reyleigh limit by digital processing or the like. Therefore, it does not become a false signal.

Further, depth information which the differential signal of the two groups of photo detectors disposed in a far field originally has is obtained simultaneously. Thus, it is possible to provide an optical resolution improvement apparatus excelling in lateral resolution and vertical resolution simultaneously, which is preferable for a laser scanning microscope.

As described above, the distance measurement system of the present invention has a structure to project two electromagnetic waves having slightly different frequencies closely to an object under measurement and use a reflected wave or a transmitted wave thereof, in which two or more detectors are disposed with a boundary line being interposed therebetween, which is located at a center of a portion where areas of the electromagnetic waves projected to the object under measurement overlap. Then, a phase difference or an intensity difference is detected from a heterodyne signal obtained by the summation signal or the difference signal from these two or more detectors.

In this manner, it becomes possible to accurately observe and measure the surface profile of the object under measurement and the thickness, the refractive index distribution, and the like of a transmissive object in an in-plane resolution less than or equal to the diffraction limit. In particular, when the difference signal is used, this effect becomes large. Accordingly, a change in the state of a cell or a microorganism, a transient change in surface state, or the like can be observed and measured.

On the other hand, when a commercialized auto-stereoscopic display, three-dimensional display using a pair of polarized glasses, or the like is used, it is also possible to display a three-dimensional image at a video rate, and thus it can be made as a useful apparatus in education, study, medical care, and the like. Further, since two beams passing through very close, substantially the same path are used, observation or measurement which is difficult to be affected by disturbance or the like can be performed.

Meanwhile, as described above, the optical resolution improvement apparatus of the present invention is an apparatus detecting the signal of a light which is converged and irradiated to a sample as an output difference of photo detectors with each other, which are symmetrical to a line including optical axes of a plurality of photo detectors disposed in a far field. Further, there is disposed an optical system effectively making all or part of the first order diffracted light and the zero order diffracted light as well as the negative first order diffracted light and the zero order diffracted light from the sample interfere with each other, so as to obtain a difference signal between the photo detectors which receive the interference intensity of each of them and are disposed symmetrically.

The optical system effectively making interference is an optical system making the zero order diffracted light and the positive and negative first order diffracted lights interfere with each other, which are converted into a parallel light, by using lenses to which the zero order diffracted light and the positive and negative first order diffracted lights are incident separately, or is an optical system, an imaging system, or a magnifying optical system shifting and overlapping the zero order diffracted light and part of the positive and negative first order diffracted lights to make them interfere with each other, by two groups of lenses having a tilted optical axis with respect to the optical axis of the zero order diffracted light. In this manner, it becomes possible to obtain a spatial frequency of 1.5 times or more as compared to an imaging optical system using a lens having the same NA. Therefore, a clear optical image can be obtained, which cannot be obtained with an ordinary imaging optical system.

Moreover, by combining with the heterodyne method, more accurate detection can be performed because of that a phase change and an intensity change can be detected quite accurately, that accurate detection is possible even when lights received by the photo detector are very weak by increasing the gain of the detection circuit system, and that the detection is not affected by disturbance lights since the signal to be detected is only a modulation signal. Therefore, it becomes possible to perform observation or measurement with a quite high resolution with respect to phase information which is very weak and low in contrast and a slight refractive index change.

BRIEF DESCRIPTION OF THE DRAWINGS

FIG. 7A is a schematic diagram of the spatial modulator and FIG. 7B is a diagram illustrating a pattern of voltage and current applied to the spatial modulator;

DETAILED DESCRIPTION OF THE PREFERRED EMBODIMENTS

Hereinafter, Embodiment 1 to Embodiment 4 of a distance measurement system according to the present invention will be described in detail based on the drawings.

Embodiment 1

Embodiment 1 of the distance measurement system according to the present invention will be described below with reference to the drawings.

Figure 1:
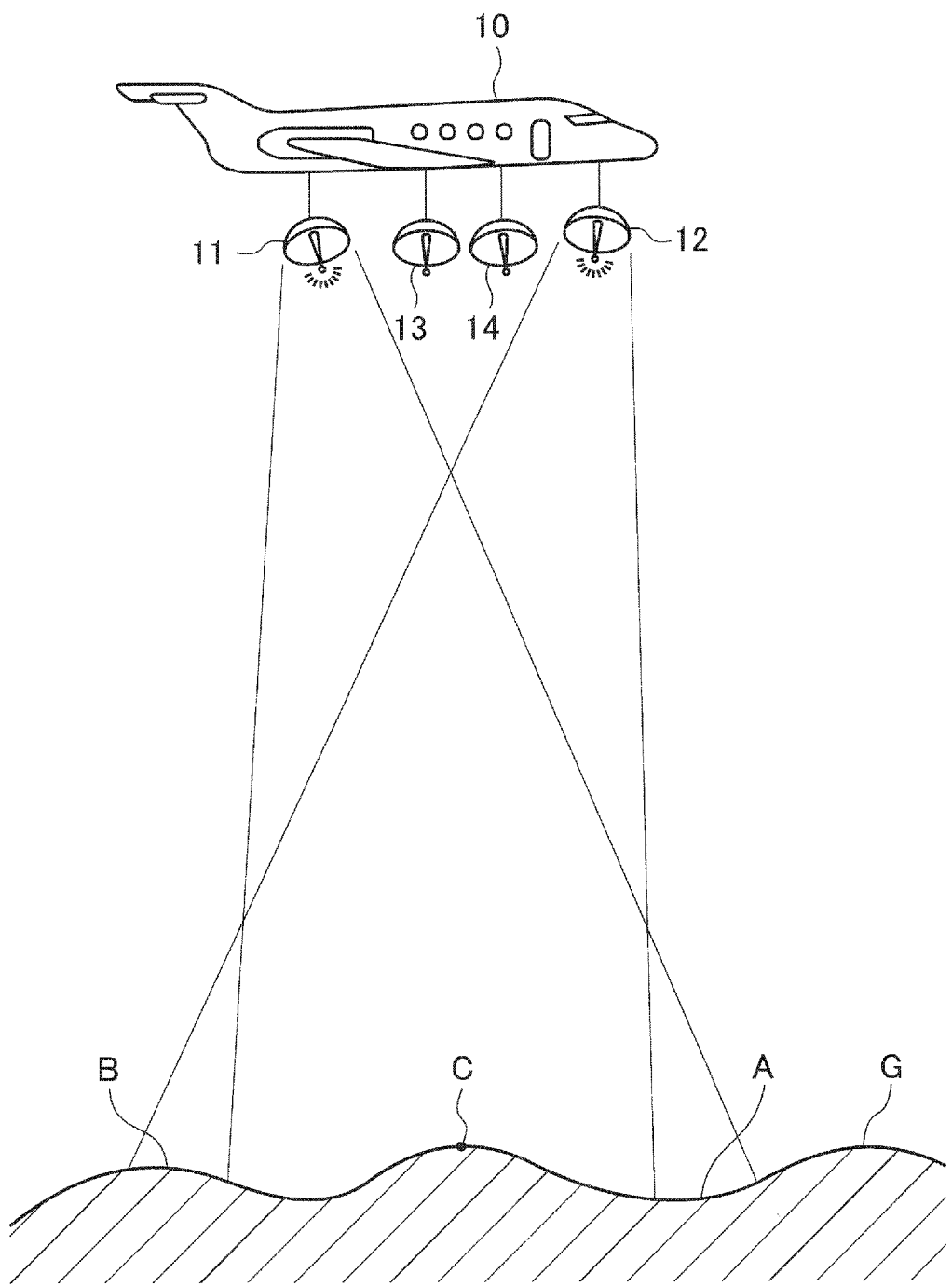
FIG. 1 is a schematic diagram illustrating Embodiment 1 related to a distance measurement system of the present invention.

FIG. 1 is a schematic diagram illustrating a structure of the distance measurement system of this embodiment. At opposite ends of an aircraft 10 illustrated in FIG. 1, a transmitting antenna 11 and a transmitting antenna 12 are mounted, each of which is a parabola antenna of microwave.

Figure 2:
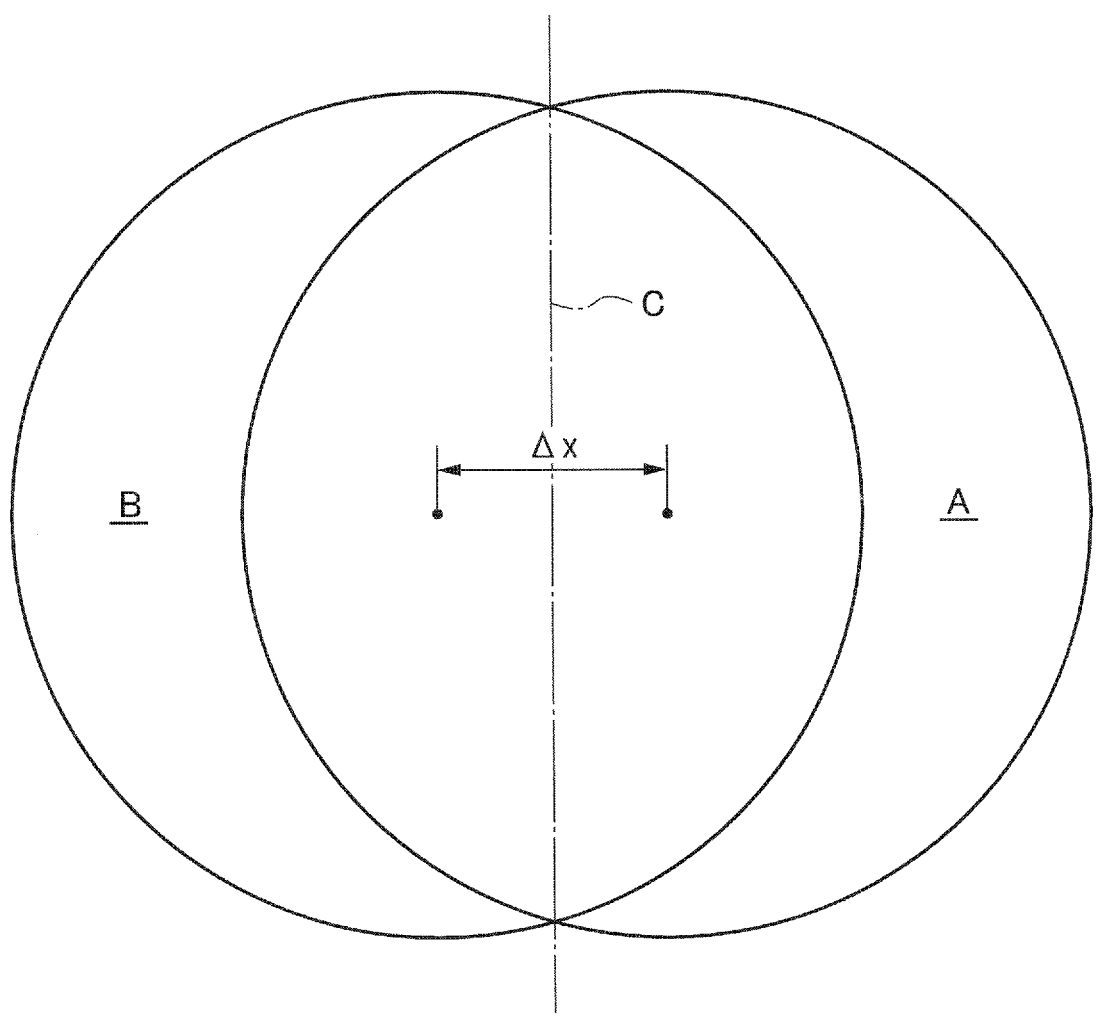
FIG. 2 is an explanatory diagram representing irradiation areas on the ground in Embodiment 1 related to the distance measurement system of the present invention.

Then, the transmitting antenna 11 and the transmitting antenna 12 of microwave, which are mounted thus on the aircraft 10, transmit transmission waves of $A \sin(2\pi(fc+fm)t)$ and $A \sin(2\pi(fc-fm)t)$ based on a carrier signal frequency fc and a modulation frequency fm to an object under measurement G of a land feature or the like, which is a three-dimensional shape on the ground, in a manner that they diverge in a conical shape of substantially the same size as each other. The respective transmission waves are irradiated to the object under measurement G on the ground in a manner that, for example, irradiation areas A, B substantially overlap but are slightly displaced by a center distance Δx by tilting the parabola antennas, as illustrated in FIG. 1 and FIG. 2.

On the other hand, on extended lines of portions located between the transmitting antenna 11 and the transmitting antenna 12 on the aircraft 10 with substantially the center of the overlapped irradiation areas A, B of the respective transmission waves being a boundary, there are disposed at least two receiving antennas 13 and 14, each of which is likewise a parabola antenna.

Specifically, the two receiving antennas 13 and 14 are capable of receiving microwaves of spatial frequencies in two directions, respectively, of the irradiation areas A, B, which are displaced from zero spatial frequency of microwaves reflected from the object under measurement G. Accordingly, respective signals received by the receiving antennas 13, 14 are a beat signal of frequency 2fm as a result of that the microwaves having two frequencies reflected from the object under measurement G are made to interfere with each other.

Figure 3:
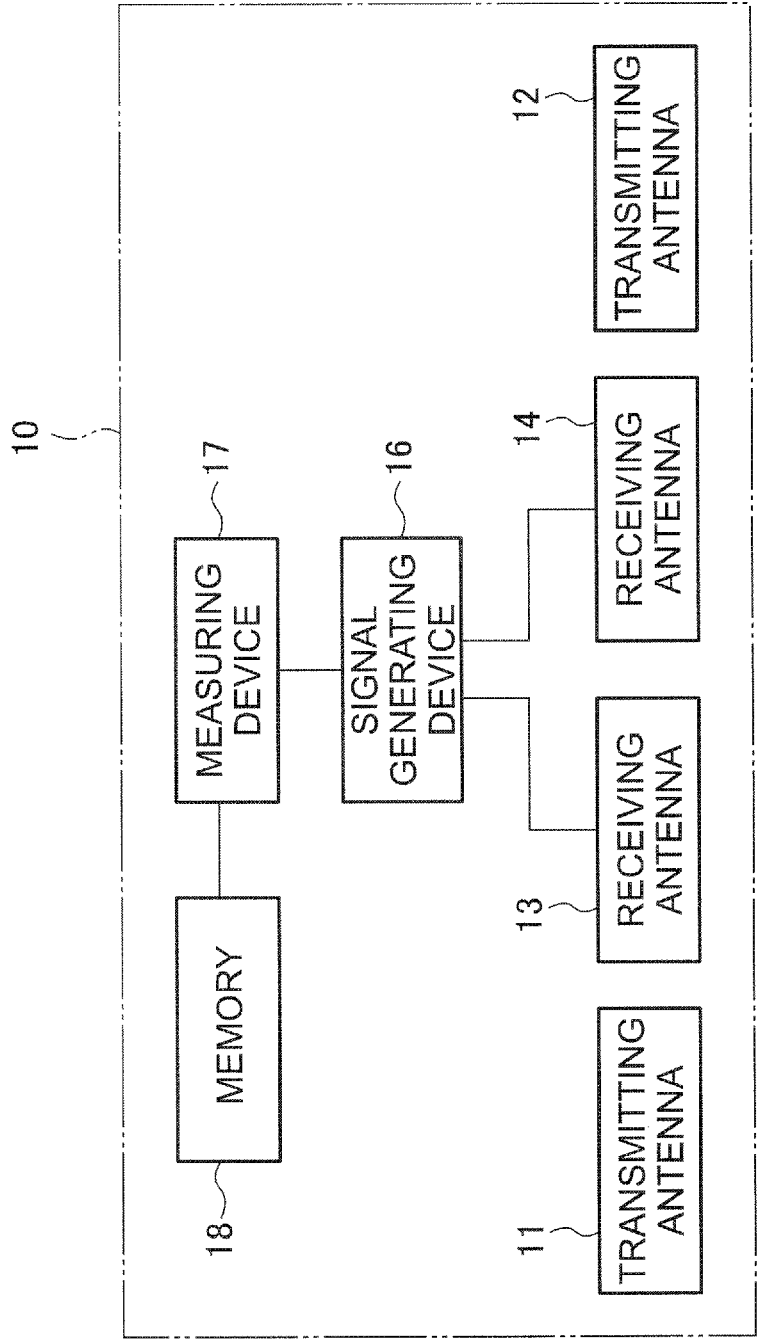
FIG. 3 is a block diagram illustrating Embodiment 1 related to the distance measurement system of the present invention.

Moreover, the aircraft has a not-illustrated transmitter or the like for transmitting the microwaves from the transmitting antennas 11, 12. Besides these antennas, in the aircraft 10 illustrated in FIG. 3, there are mounted a signal generating device 16 as a signal generating means for generating a summation signal or a difference signal based on signals received by the receiving antennas 13, 14, a measuring device 17 as a measuring means for measuring the height of the aircraft 10, or the like from a phase displacement of these signals, and a memory 18 such as a hard disk drive which stores height data, and the like.

Here, when a phase displacement is detected by using the summation signal or the difference signal of signals received by the receiving antenna 13 and the receiving antenna 14, height information of the two irradiation areas A, B can be obtained. Specifically, the signal generating device 16 generates the summation signal of the receiving antennas 13, 14 or the difference signal of the receiving antennas 13, 14 from each other and obtains a slight frequency difference (beat signal) based on these signals, and the measuring device 17 measures the phase displacement thereof from an inputted signal.

Then, accompanying that the resolution of about a fraction of a wavelength is obtained from the summation signal in the measuring device 17, height information as a distance between the aircraft 10 having the receiving antennas 13, 14 and the object under measurement G can be obtained with this resolution. Further, when the difference signal is used in the measuring device 17, only the portion in which the phase difference has occurred contributes to the phase difference as compared to the case of the summation signal, and thus the resolution becomes high and the sensitivity increases significantly.

Note that although the number of aforementioned receiving antennas is two in this embodiment, three or more receiving antennas may be mounted. Further, when a transmitter is mounted instead of the signal generating device 16, the measuring device 17, and the memory 18, these signal generating device 16, measuring device 17, and memory 18 may be placed on the ground.

The principle of operation of this distance measurement system will be described in detail below.

It is assumed that the center distance $\Delta x$ between the irradiation areas A, B of the two microwaves illustrated in FIG. 2 is set less than or equal to the diffraction limit which the microwaves have. In this case, the irradiation areas A, B of the respective microwaves would not be less than or equal to the diffraction limit of the Abbe's theory, but since they are microwaves of respective different frequencies which are displaced slightly, differential information can be obtained by heterodyne detecting these microwaves. At that time, when the summation signal of the receiving antenna 13 and the receiving antenna 14 is used, it is substantially equivalent to a differential interference microscope, which is one kind of optical microscope, and when the difference signal thereof is used, a much higher lateral resolution can be obtained than the differential interference microscope.

For simplicity, it is considered in one dimension. First, a phase distribution of a profile d(x) of the object under measurement G located on the ground or the sea is assumed as $Ae^{j\theta(x)}$. Here, $\theta(x)=2\pi d(x)/\lambda$. In the case of reflection as in this embodiment, the path difference becomes double, and thus a half of observed $\theta(x)$ may be assumed as the height information.

As described above, the center distance between the irradiation areas A, B of the two microwaves on the object under measurement G is $\Delta x$, and a complex amplitude distribution of microwaves on the ground or the sea is u(x). In this case, at a sufficiently distant location as compared to the object under measurement G, it is a Fourier transform of the product of the profile of the object under measurement G and a beam profile.

In this distance measurement system, the microwave received by one receiving antenna is modulated with $e^{j(\omega c-\omega m)t}$, and the microwave received by the other receiving antenna disposed separately at the center distance $\Delta x$ is modulated with $e^{j(\omega c+\omega m)t}$.

Therefore, the complex amplitude distribution E on the receiving antennas 13, 14 becomes as follows.

$$E = \int (Ae^{j\theta(x)}u(x)e^{jkx}dx \cdot e^{j(\omega c-\omega m)t} + Ae^{j\theta(x+\Delta x)}u(x)e^{jkx}dx \cdot e^{j(\omega c+\omega m)t})$$

When detection of intensity I is performed with these receiving antennas 13, 14, the heterodyne detection of I=EE* and moreover $2\omega m$ is performed, and thus it is as following Equation (4).

$$I(k) = A^2 \int e^{j(\theta(x)-\theta(x'+\Delta x'))}u(x)u(x')e^{jk(x-x')}dxdx'e^{-j2\omega mt} + A^2 \int e^{-j(\theta(x)-\theta(x'+\Delta x'))}u(x)u(x')e^{jk(x-x')}dxdx'e^{j2\omega mt}$$

Equation (4)

Then, substantially the center of the overlapped irradiation areas A, B of the two microwaves is assumed as the boundary line C of FIG. 1 and FIG. 2, and the two receiving antennas 13, 14 are disposed separately from the object under measurement and corresponding to positions with this boundary line C being interposed therebetween, the positions along the separation direction of the respective irradiation areas A, B. Here, first, what the summation signal of the signals received by the two receiving antennas 13, 14 would be is considered. At the positions distant from the object under measurement, it can be considered as a Fourier transform plane. Thus, when the maximum spatial frequency which can be received by the receiving antenna is Kmax, the intensity I can be obtained with the summation signal from the following equation.

$$I = \int I(k)dk \text{(the range of integral is } -K\text{max to } K\text{max)}$$
$$= A^2 \int \cos(\theta(x)-\theta(x'+\Delta x')-2\omega mt)u(x)u(x')\sin(K\text{max}(x-x'))/(x-x')dxdx'$$

When the receiving antenna is enlarged and disposed so as to receive up to a wide spatial frequency, $\sin(K\text{max}(x-x'))/(x-x')=K\delta(x-x')$ holds, and thus the intensity is as following Equation (5).

$$I=A^2\int \cos(\theta(x)-\theta(x+\Delta x)-2\omega mt)u(x)^2 dx \quad \text{Equation (5)}$$

That is, the phase difference of the separated positions of the two microwaves is integrated with the weight of the profiles of the microwaves.

By transforming Equation (5), the following equations are obtained.

$$Iq=A^2\int \cos(\theta(x)-\theta(x+\Delta x))u(x)^2 dx \cdot \cos(2\omega mt)$$

$$Ii=A^2\int \sin(\theta(x)-\theta(x+\Delta x))u(x)^2 dx \cdot \sin(2\omega mt)$$

Therefore, by an orthogonal transformation, the obtained phase difference $\Theta$ becomes as following Equation (6).

$$\theta=\tan^{-1}(\int \sin(\theta(x)-\theta(x+\Delta x))u(x)^2 dx/\int \cos(\theta(x)-\theta(x+\Delta x))u(x)^2 dx) \quad \text{Equation (6)}$$

On the other hand, considering the difference signal of the two receiving antennas 13, 14, the following equation can be obtained similarly to the case of the summation signal.

$$I = \int I(k)dk \text{ (the range of integral is 0 to } K\text{max)} -$$

$$\int I(k)dk \text{ (the range of integral is } -K\text{max to 0)}$$

$$= A^2 \int \sin(\theta(x) - \theta(x' + \Delta x') - 2\omega mt)u(x)u(x')(\cos(K\max(x-x'))-1)/$$

$$(x-x')dxdx'$$

When the receiving antenna is enlarged and disposed so as to receive up to a wide spatial frequency, $(\cos(K\max(x-x'))-1)/(x-x')=\delta(x-x')+1/x(\delta(x)-1)$ holds, and thus the intensity is as following Equation (7).

$$I = A^2 \int d/dx(\sin(\theta(x)-\theta(x+\Delta x)-2\omega mt))u(x)^2 dx \quad \text{Equation (7)}$$

Moreover, by transforming Equation (7), the following equations can be obtained.

$$Iq = A^2 \int d/dx(\sin(\theta(x)-\theta(x+\Delta x))u(x)^2 dx \cdot \cos(2\omega mt)$$

$$Ii = A^2 \int d/dx(\cos(\theta(x)-\theta(x+\Delta x))u(x)^2 dx \cdot \sin(2\omega mt)$$

Therefore, by an orthogonal transformation, the obtained phase difference Θ becomes as following Equation (8).

$$\Theta = \tan^{-1}(-\int d/dx(\cos(\theta(x)-\theta(x+\Delta x))u(x)^2 dx/\int d/dx(\sin(\theta(x)-\theta(x+\Delta x))u(x)^2 dx) \quad \text{Equation (8)}$$

Here, Equation (6) and Equation (8) are compared. Qualitatively, the following points can be understood.

First, Equation (6) represents the phase difference which can be obtained as a result of smoothing with a weighting function of u(x) the phase difference of two points separated by the center distance Δx of the irradiation areas A, B, and thus represents an average phase difference in the irradiation areas A, B. This is processing equivalent to the differential interference microscope.

On the other hand, in Equation (8), a differential of the phase difference of the two points separated by the center distance Δx of the irradiation areas A, B is smoothed with the weighting function of u(x), and thus the original function is restored approximately.

Therefore, when the aircraft 10 makes a flight, the phase difference and the position information can be obtained with the lateral resolution equivalent to the degree of separation of the irradiation areas A, B.

Here, the case where the two receiving antennas are disposed has been described. However, a similar result can be obtained when a plurality of array antennas are disposed separately from the object under measurement G along the separation direction of the two microwaves in the vicinity of the centers of the overlapped areas of the irradiation areas A, B. In particular, when a difference output is to be obtained, a difference operation may be performed between the corresponding antennas among the plurality of array antennas disposed corresponding to the vicinity of the centers of the overlapped portions of the irradiation areas A, B.

Further, when only the summation output of the plurality of array antennas is used, a similar operation can be realized by substantially using one receiving antenna.

Note that for the simplicity of explanation, the equations are simplified on the assumption that the spatial frequency to be obtained is wide, but when the spatial frequency which can be obtained is not large, the portion of the δ function in the equations just becomes a convolution, and the fact remains that the resolution improves essentially. In this case, some blur occurs in the profile and the like of the object under measurement G.

The above description is given in detail with respect to the phase, but a similar description can be given with respect to the intensity. In particular, with respect to the change in profile smaller than the irradiation areas A, B, the pattern in a far field of interference fringes formed by interference of a zero order diffraction wave and a first order diffraction wave of Fourier is transform in an area being irradiated is different between the two receiving antennas 13, 14. Accordingly, the difference signal of the receiving antennas 13, 14 appears as an intensity difference reflected on a tilt of the profile.

As described above, by using the heterodyne detection to process spatial frequency information on the Fourier transform plane, quite high improvement in lateral resolution can be provided particularly by the difference operation.

Embodiment 2

The concept of Embodiment 2 of a distance measurement system according to the present invention will be described below.

A coherent light like a laser emitted from a light source is modulated into two lights with substantially different frequencies by an acoustic optical device or a spatial modulator as a first means. At that time, when the acoustic optical device is used for example, diffraction bands are modulated by interaction of a surface acoustic wave of this acoustic optical device and the lights. A Doppler shifted light undergoes frequency modulation, and is emitted as a diffracted light of the positive or negative first order. On the other hand, when the spatial light modulator is used, a similar effect can be provided by modulating diffraction bands written in this spatial light modulator.

Thus, the frequency modulated lights are separated into two lights close to each other and meanwhile emitted from the first means. These two lights are two-dimensionally scanned by a pupil-transmission optical system, a two-dimensional scanning device, or the like as a second means and are irradiated to the object under measurement by an objective lens, or the like as a third means. Photo detectors disposed at positions distant from this object under measurement in a manner of being divided in two along the separation direction of two lights are a fourth means. The photo detectors respectively receive lights reflected from the object under measurement or transmitted through the object under measurement as lights with the boundary line being interposed therebetween to extend in a direction substantially perpendicular to the separation direction of the two lights.

The lights which are received by the photo detectors in this manner are photoelectrically converted, and in a signal comparator as a fifth means, the difference signal or the summation signal of respective outputs is generated, which are located at symmetrical positions with a direction substantially perpendicular to the separation direction of the two lights being a boundary line. This difference signal or summation signal is heterodyne detected in a data processing unit as a sixth means, to thereby detect a phase difference or detect an intensity difference.

This detected phase difference or intensity difference indicates height information of the profile of a surface of the object under measurement in the case of reflection, or indicates information of a thickness, a refractive index distribution, or the like in the case of transmission. At this time, the irradiation areas A, B of microwaves described in Example 1 may be considered as a diffraction limit spot diameter, which is narrowed down by the objective lens. Specifically, the heterodyne detection based on the summation signal of the respective photoelectrically converted signals indicates the phase difference obtained as a result of smoothing with the weighting function of u(x) the phase difference between two points separated by the center distance of beams, which are the two lights. Accordingly, the heterodyne detection based on this summation signal indicates an average phase difference in the beams, and this is processing equivalent to the differential interference microscope.

On the other hand, in the heterodyne detection based on the difference signal of the respective photoelectrically converted signals, the differential of the phase difference of two points separated by the center distance of the beams is smoothed with the weighting function of u(x), and thus the original function is restored approximately.

Thus, when beams are scanned with the pupil-transmission optical system, it is possible to obtain the phase difference and the position information with the lateral resolution equivalent to the degree of separation of the beams.

In the foregoing, the case of applying the photo detectors divided in two with an optical axis being a boundary line has been described. However, the same applies in the case where a plurality of photo detectors are disposed separately from the object under measurement along the separation direction of the beam. In particular, when the difference output is to be obtained, it may be obtained by photo detectors which are adjacent across a boundary line. Further, when only the summation output of the plurality of photo detectors is used, the same can be realized substantially by using one photo detector.

Then, when a tilt of the profile of the object under measurement exists in the beams, the direction in which the lights are reflected or transmitted is different quantitatively, and thus a difference output as intensity is given to the two photo detectors. Describing more specifically, when a change in profile smaller than a beam diameter occurs, the pattern in a far field of interference fringes formed by interference of a zero order diffraction wave and a first order diffraction wave of Fourier transform in an area being irradiated with the lights is different between the two photo detectors. Accordingly, the difference signal of the two photo detectors appears as an intensity difference reflected on the tilt of the profile.

Hereinafter, Embodiment 2 of the distance measurement system according to the present invention will be described specifically using the drawings.

Figure 4:
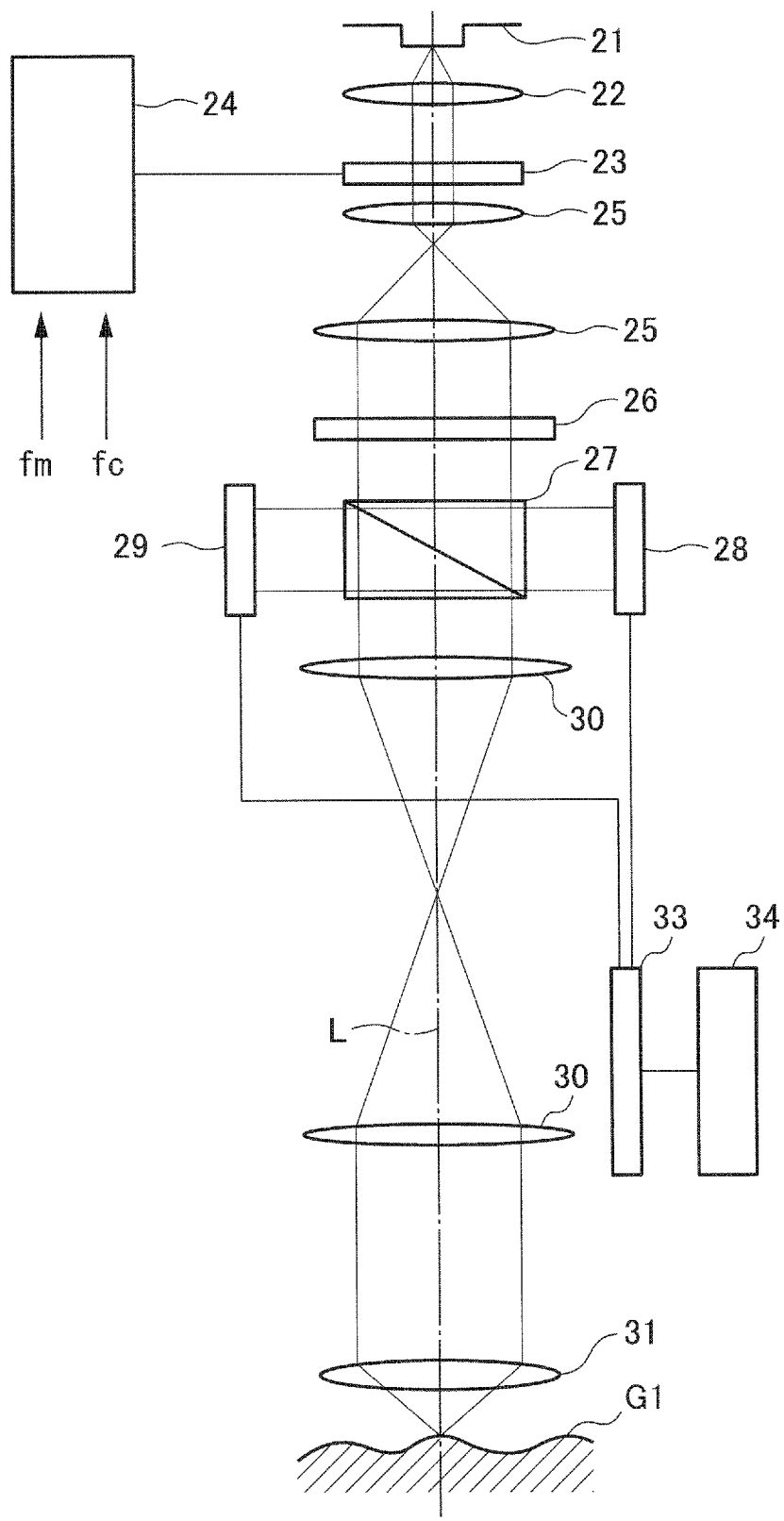
FIG. 4 is a block diagram of an optical system illustrating Embodiment 2 related to the distance measurement system of the present invention.

FIG. 4 is a block diagram illustrating a structure of the distance measurement system according to this embodiment. As illustrated in FIG. 4, a collimator lens 22 is disposed between a laser light source 21 as a light source emitting a laser light and an acoustic optical device (AOD) 23 as the first means, which is controlled in operation by an AOD driver 24 connected thereto.

Further, a pupil transmission magnifying lens system 25 constituted of two groups of lenses, a two-dimensional scanning device 26 which two-dimensionally scans inputted laser lights, and a polarized beam splitter 27 which separates and emits inputted laser lights are disposed sequentially in line with the acoustic optical device 23. However, the pupil transmission magnifying lens system 25, the beam splitter 27, and the two-dimensional scanning device 26 may be disposed sequentially in line with the acoustic optical device 23.

Moreover, a pupil transmission lens system 30 constituted of two groups of lenses is located adjacent to this polarized beam splitter 27, and an objective lens 31 is disposed adjacent thereto opposing an object under measurement G1. That is, these members are lined up along an optical axis L. On the other hand, a photo detector 28 and a photo detector 29, each of which is a light sensor, are disposed at both adjacent positions of the polarized beam splitter 27 in a direction orthogonal to the direction in which the optical axis L passes.

These photo detectors 28, 29 are both connected to a signal comparator 33 which compares signals from these photo detectors 28, 29, and this signal comparator 33 is connected to a data processing unit 34 which finally processes data to obtain the profile and so on of the object under measurement G1.

Further, the laser light source 21 is a gas laser of He—Ne or the like, a semiconductor laser, or a solid laser, and generates a coherent laser light.

This laser light is converted into a parallel luminous flux by the collimator lens 22, which is made to be incident on the acoustic optical device 23. At this time, the incident beam diameter of the laser light is made appropriate in relation with the pupil transmission magnifying lens system 25 in a later stage by using an aperture mechanism (not illustrated) or the like. Moreover, a DSB modulation signal such as $\sin(2\pi fct) \sin(2\pi fmt)$ is applied as a modulation signal to this acoustic optical device 23 by the AOD driver 24.

When such a modulation is performed, the acoustic optical device 23, to which two frequency modulations of fc+fm and fc−fm are applied, generates a compression wave of acoustic wave equivalent to pitch d of a Bragg diffraction grating. That is, when the velocity of the acoustic wave is Va and the frequency to be applied is f, d=Va/f holds. Specifically, by this compression wave, a beam which is a laser light incident on the acoustic optical device 23 is separated into a positive and negative first order diffracted lights, and each of the diffracted lights is modulated with a frequency fc±fm. For example, $TeO_2$ is used as the material for the acoustic optical device 23, and the acoustic velocity of this material is 660 m/s.

When 40 MHz is chosen as the frequency fc of a carrier frequency, this results in d=16.5 μm, and when the laser light source 21 is used as the He—Ne laser, the angle of diffraction θ becomes an angle of approximately 2.19791 degrees. In FIG. 4, the structure is illustrated so that the optical axis L does not change, but in practice, the optical system beyond the acoustic optical device 23 is tilted in advance by the angle of diffraction θ, or a bias is applied to the two-dimensional scanning device 26 in advance so as to effectively give the tilt of the angle of diffraction θ.

When the frequency fm of about 10 KHz is added to this carrier frequency, the positive and negative first order diffracted lights are θ=2.19847 degrees and θ=2.19737 degrees and are modulated by 40.01 MHz and 39.99 MHz, respectively. When the laser lights are made to be incident on the objective lens 31 while keeping these angles, if the objective lens 31 has a focal length of 2 mm and NA of 0.9, the center distance of the beams is approximately 0.6 and the diffraction limit at that time is w=0.857 μm. Specifically, the degree of separation of the beams is thus set smaller than the diffraction limit system.

Note that the resolution can be improved when the degree of separation of the beams, which is the center distance of the beams, is set smaller, but when the frequency of the heterodyne detection is decreased, the processing speed becomes slow. In this case, using an acoustic optical device with a faster acoustic velocity can increase the pitch d of the Bragg diffraction grating, and thus the processing speed can be improved. In practice, ones with an acoustic velocity Va of about 4.2E+3 m/s are known and commercially available.

Here, the pupil transmission magnifying lens system 25 disposed between the acoustic optical device 23 and the polarized beam splitter 27 is an optical system for transmitting an emission surface position of the acoustic optical device 23 in a conjugate manner to the next two-dimensional scanning device 26. The lights passing through this pupil transmission magnifying lens system 25 are transmitted to the two-dimensional scanning device 26, and through the pupil transmission lens system 30, which is conjugate to the pupil position of the objective lens 31, the lights from this two-dimensional scanning device 26 are incident on the objective lens 31 as the positive and negative first order diffracted lights having an angle difference.

Specifically, by inputting the two DSB-modulated signals of carrier frequency fc and modulation frequency fm to the acoustic optical device 23 from the outside via the AOD driver 24, these two quite close luminous fluxes can be generated.

Then, luminous fluxes emitted in two quite close directions are incident on the objective lens 31 through the pupil transmission lens system 25 transmitting the substantial pupil position of the acoustic optical device 23 to the pupil position of the two-dimensional scanning device 26 as described above, the two-dimensional scanning device 26 scanning the lights on a surface, and the pupil transmission lens system 30 for transmitting the pupil position of the two-dimensional scanning device 26 to the pupil of the objective lens 31.

Figure 5:
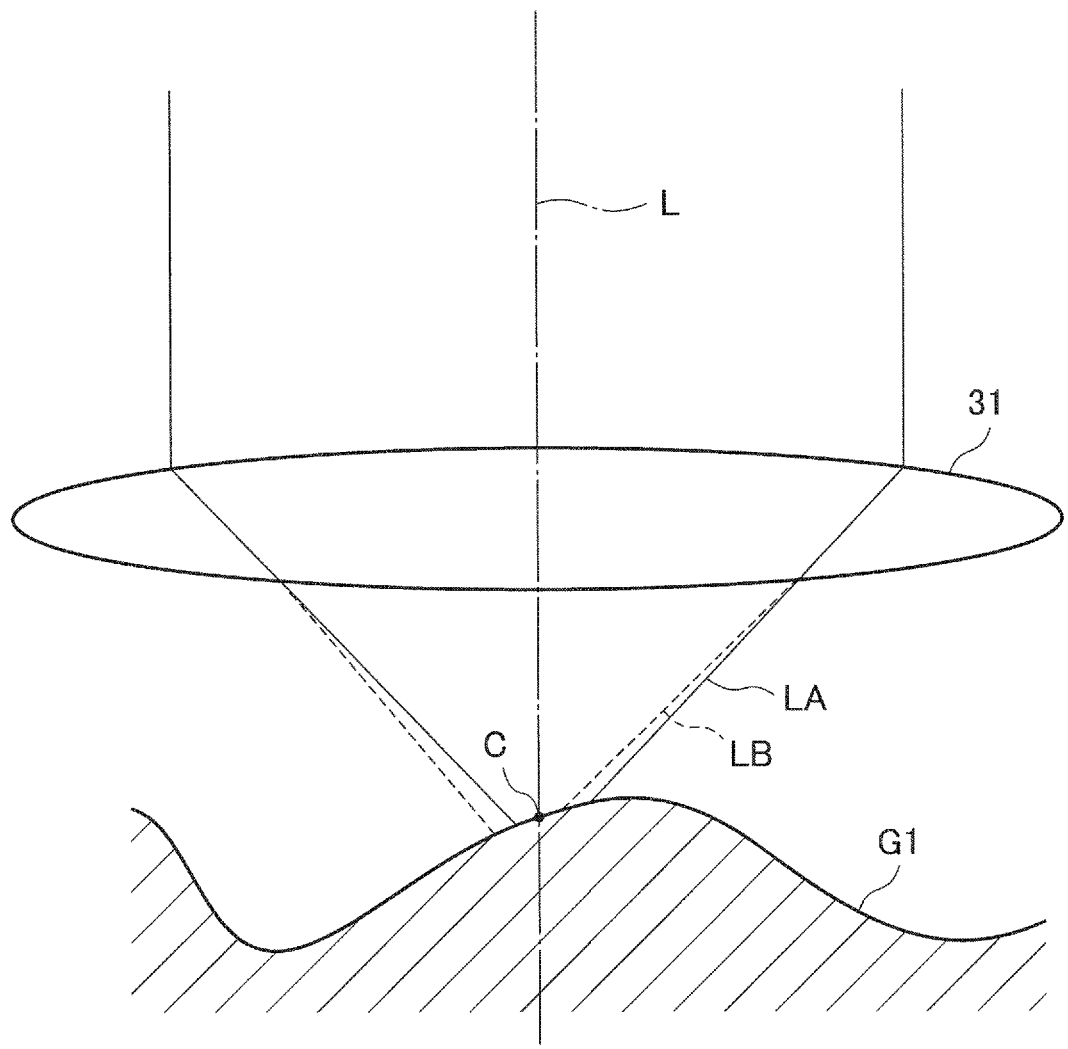
FIG. 5 is a diagram illustrating in magnification an objective lens of FIG. 4 and a portion in the vicinity of an object under measurement.

Thus, two very close beams having the same diameter as each other can be obtained, like a beam LA denoted by a solid line and a beam LB denoted by a dotted line in FIG. 5.

As a result, the beams LA, LB which are luminous fluxes converged through the objective lens 31 scan the surface of the object under measurement G1 as two quite close spots. These two spots become the two signals of the frequency fc+fm and the frequency fc−fm, and thus by heterodyne detecting these signals, signals reflecting concave and convex information and a refractive index distribution of the object under measurement G1 can be obtained.

Further, the frequencies which these two beams LA, LB have are "vibration frequency of light+carrier frequency fc±modulation frequency fm." When the center distance of the two close beams is set equal to or less than the diffraction limit as described above, the respective beams would not be equal to or less than the diffraction limit of the Abbe's theory. However, since they are lights with different frequencies slightly displaced from each other, differential information can be obtained by performing the heterodyne detection. Moreover, the photo detector 29 illustrated in FIG. 4 is constituted of photo detectors divided in two or more elements. Then, with the optical axis L being a boundary line, these photo detectors are disposed so as to have a dark line in the direction perpendicular to the separation direction of the beams with this boundary line being interposed therebetween, and the beat signal is obtained from the summation signal or the difference signal thereof. At that time, when the summation signal is used, it is substantially equivalent to a differential interference microscope, and when the difference signal is used, a much higher lateral resolution can be obtained.

Here, the nature of lights to be irradiated to the object under measurement G1 will be described specifically. The lights narrowed down by the objective lens 31 become two close beams LA, LB as illustrated in FIG. 5, which are irradiated to the object under measurement G1. Note that the complex amplitude Ea of the beam LA and the complex amplitude Eb of the beam LB are as the following equations.

$$Ea = A\exp j(2\pi(fo+fc+fm)t)$$

$$Eb = B\exp j(2\pi(fo+fc+fm)t+\delta)$$

Here, δ in the equation of the complex amplitude Eb represents a phase difference in a height direction of the beam LB with reference to the beam LA, and fo represents the frequency of the light. Note that as described above, the interval between these two beams is determined by the modulation frequency fm applied to the acoustic optical device 23, and thus is irrelevant to the scanning speed.

These two beams LA, LB reflected by the object under measurement G1 illustrated in FIG. 4 and FIG. 5 are guided to the photo detector 29 via the objective lens 31, the pupil transmission lens system 30, and the polarized beam splitter 27. When the photo detector 29 is disposed at a position conjugate to the position of the two-dimensional scanning device 26, the two beams LA, LB return to the same position, and thus the phase difference δ of the two beams LA, LB is detected as the beat signal.

That is, this photo detector 29 has a structure having a not-illustrated photoelectric conversion unit, and the intensity I of the two beams LA, LB on the photo detector 29 is detected by the photoelectric conversion unit of the photo detector 29 with a value based on the following equation, and is sent to the signal comparator 33.

$$I = (Ea+Eb)(Ea+Eb)^* = A^2 + B^2 + 2AB\cos(2\pi^* 2fmt + \delta)$$

Accompanying this, by performing a phase comparison of the heterodyne detection of the frequency 2fm using the signal comparator 33 illustrated in FIG. 4, the phase difference δ can be measured. Thus, the is position information is obtained.

Now, the photo detector 28 disposed to oppose the photo detector 29 across the polarized beam splitter 27 also has a structure having a not-illustrated photoelectric conversion unit. Then, the beat signal of the incident beam of the diffracted light generated in the acoustic optical device 23 is made to be incident on this photo detector 28, and is detected by the photoelectric conversion unit of the photo detector 28. That is, the phase difference generated in the optical system or the like from the acoustic optical device 23 is detected by the photoelectric conversion unit of the photo detector 28, and hence the photo detector 28 serves a role of giving the reference for phases.

On the other hand, in the photo detector 29 as described above, the beat signal to which the phase difference information between the two beams, the beam LA and the beam LB, is added is detected by the photoelectric conversion unit in the photo detector 29, and is sent to the signal comparator 33. Therefore, by performing a comparison of these two phases in the signal comparator 33, the true phase difference δ is detected. This true phase difference δ is δh=λδ/4π, which is the average phase difference of the beam LA and the beam LB, that is, the difference information of the average height h. Here, λ represents the wavelength of the laser light emitted from the laser light source 21.

When the information is sent to the data processing unit 34 constituted of a CPU, a memory, and so on and connected to the signal comparator 33, this information is recorded together with scanning information of a flat surface in the data processing unit 34, and profile information of the surface of the object under measurement G1 can be derived easily. Further, when faster data are to be obtained, this can be realized by using the acoustic optical device 23 having the velocity Va that is as high as possible.

On the other hand, to perform the heterodyne detection in this embodiment, part of the irradiated modulation signal is taken out by the beam splitter 27, and a reference signal is obtained in the photo detector 28. Then, a differential output is obtained from this reference signal and the signal detected in the photo detector 29 divided in two, and the phase difference information and the intensity information are obtained by the signal comparator 33, which are then sent to the data processing unit 34.

In the data processing unit 34, the information obtained together with the scanning information is displayed in the form of an image or data on a display, or stored as data in the memory.

However, the photo detector 28 is not always necessary, and a comparison may be performed with a signal outputted to the acoustic optical device 23, that is, a signal itself applied to the acoustic optical device 23. In this case, a delay due to the circuit system, the acoustic optical device, or the like occurs, but performing correction of this delay in advance, or the like can prevent it from largely affecting the phase difference detection, and so on.

Further, the two quite close spot lights scanning the surface of the object under measurement G1 are lights having different frequencies from each other. However, substantially, quite close spots can be made even with high frequencies by using a magnifying optical system such as the pupil transmission lens system 25, 30, or the like. Thus, high-speed information obtainment by high-speed scanning can be performed.

From the foregoing, by using the optical system of the distance measurement system of this embodiment as described above, it is possible to obtain three-dimensional measurement data every time two-dimensional scanning is performed. Accordingly, by using the distance measurement system of this embodiment, a change in the state of a cell or a microorganism, a transient change in surface state, or the like can be observed and measured at high speed.

On the other hand, the two lights obtained in this manner can be given a very small degree of separation by the above-described method, and have substantially no difference from information scanned by one beam. In contrast, the method to scan with one beam and obtain the differential output of the photo detector, which is divided at least in two and disposed in a far field, is the above-described DPC method.

That is, as compared to the DPC method, in such a method further using this heterodyne method, more accurate detection can be performed because of that a phase change and an intensity change can be detected quite accurately by performing the heterodyne detection, that accurate detection is possible even when lights received by the photo detector 29 are very weak by increasing the gain of the detection circuit system, and that the detection is not affected by disturbance lights since the signal to be detected is only a modulation signal.

Further, it is also possible to display a three-dimensional image by using a commercialized auto-stereoscopic display, three-dimensional display using a pair of polarized glasses, or the like, and thus it can be made as a useful apparatus in education, study, medical care, and the like. Since the degree of overlap of the two beams at that time is smaller than the beam diameter, almost no path difference occurs in the two beams. From this point, the influence of disturbance and vibration occurs simultaneously in the two beams, and thus the influence of them is canceled out.

On the other hand, in this embodiment, an example is illustrated in which the degree of separation of the beams is made much smaller than the individual beam diameters. However, the optical system of the present invention is useful even in the case where, by increasing the modulation frequency, the degree of separation of the beams becomes large, and the degree of separation to the extent of the beam diameter is needed.

Note that although an example of using the two-dimensional scanning device is described in this embodiment, in an application which needs simple data of only one direction, similar effects can be obtained when this two-dimensional scanning device is replaced with a one-dimensional scanning device. As the one-dimensional scanning device, a galvano mirror, a resonant mirror, a rotating polygon mirror, or the like can be employed. Further, the two-dimensional scanning device can be realized by preparing two above-described one-dimensional scanning devices for X direction and Y direction, and interposing a pupil transmission lens system therein. Further, a micro-mirror device using the technology of micro-machine may be employed. As this micro-mirror device, ones for both one-dimensional use and two-dimensional use are known and commercialized.

As described above, by processing spatial frequency information on a Fourier transform plane, quite large improvement in lateral resolution can be achieved particularly in difference operation. Further, as described above, the point that the intensity difference signal is data reflecting the height of profile data is also the same.

Embodiment 3

This is an embodiment in the case where the reflective optical system described in Embodiment 2 is replaced with a transmissive optical system.

Figure 6:
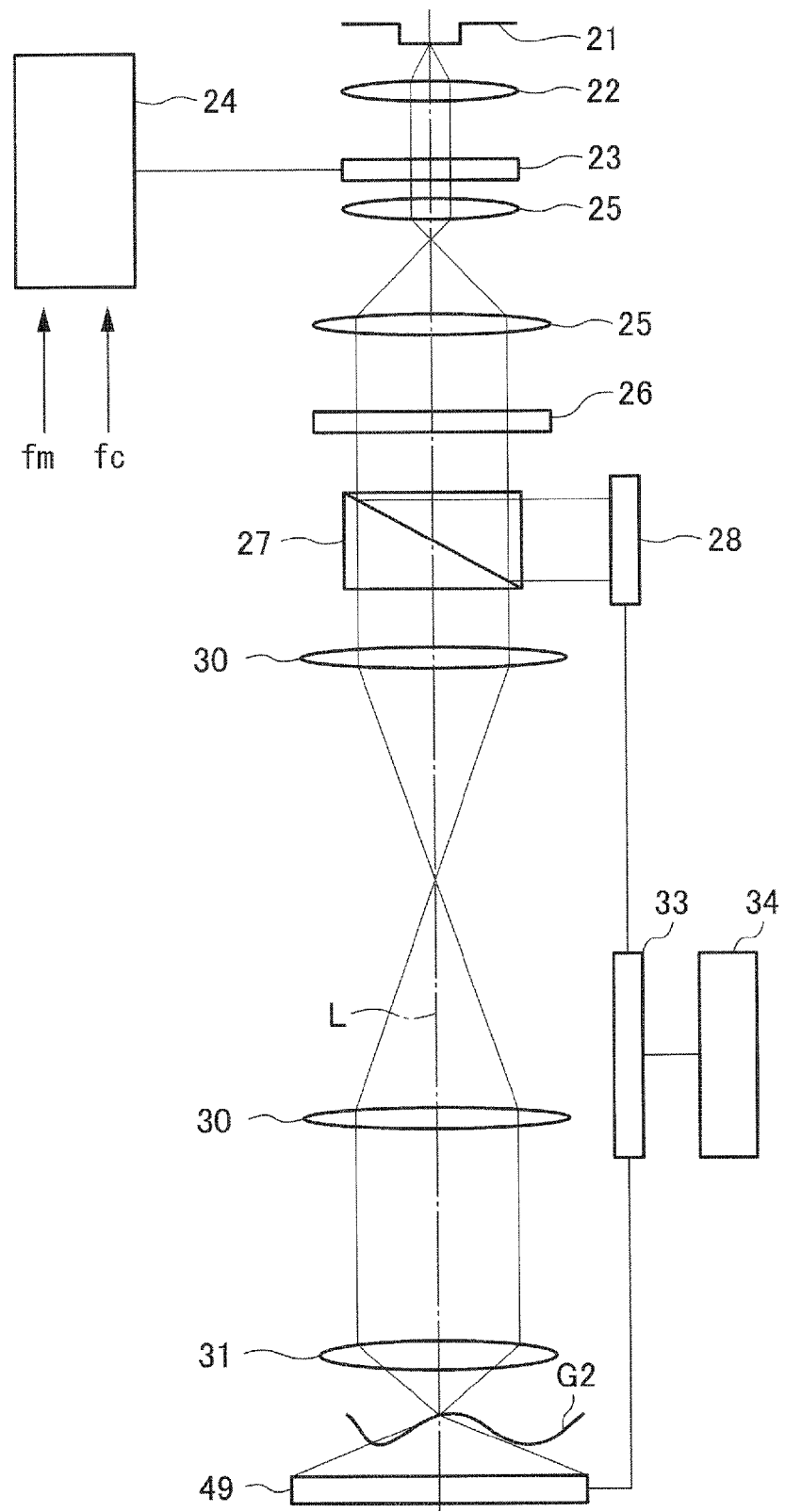
FIG. 6 is a block diagram of an optical system illustrating Embodiment 3 related to the distance measurement system of the present invention.

FIG. 6 is a block diagram illustrating a distance measurement system using a transmission type optical system according to this embodiment. The major part of the optical system is the same as in Embodiment 2 and hence is omitted from description. In this embodiment, as illustrated in FIG. 6, the lights gathered at the objective lens 31 transmit an object under measurement G2. Accordingly, it is characterized in that a photo detector 49 is disposed on the side opposite to the objective lens 31 across the object under measurement G2. That is, in the case of this embodiment, the photo detector 49, which is divided in the form that a dark line extends in a perpendicular direction to the separation direction of two beams, is disposed on an extended line of the optical axis L of the objective lens 31.

From the above, according to this embodiment, as compared to the reflection type optical system, the photo detector 49 can be disposed closely to the object under measurement G2, and thus it is possible to set the spatial frequency which can be obtained to a very high frequency. As a result, reproducibility of the spatial frequency which the object under measurement G2 has becomes good, and thus further improvement in lateral resolution becomes possible. In particular, observation or measurement of a living organism, a cell, or the like in a living state can be performed at a very high resolution. This is a quite different characteristic from a measuring device which has a high magnification but is only able to perform observation of a living organism in a dead state, such as an electron microscope.

Embodiment 4

This embodiment is characterized in that as a member for applying modulation, a spatial modulator is used as a substitute for the acoustic optical device 23.

Figure 7A:
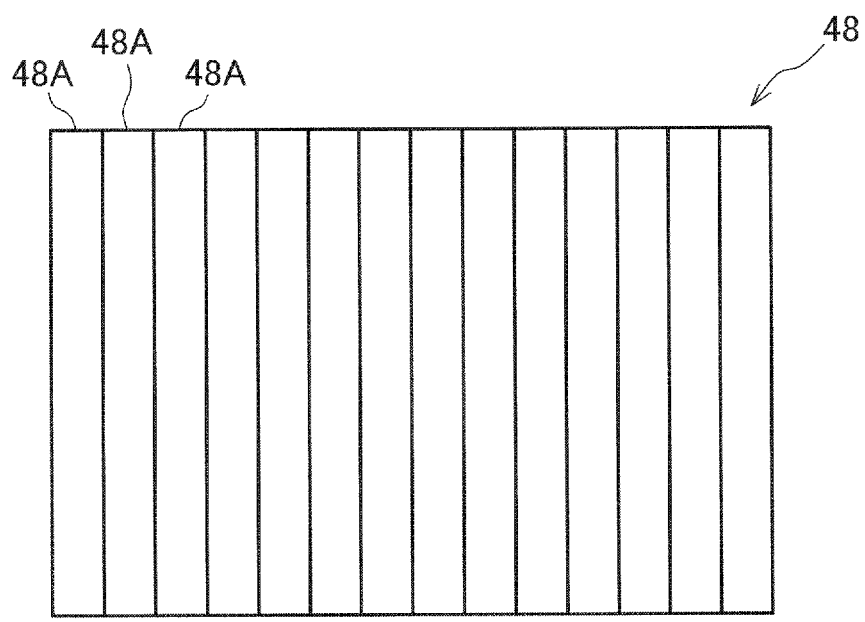
FIGS. 7A and 7B are diagrams illustrating a spatial modulator applied to Embodiment 4 related to the distance measurement system of the present invention, where
Figure 7B:
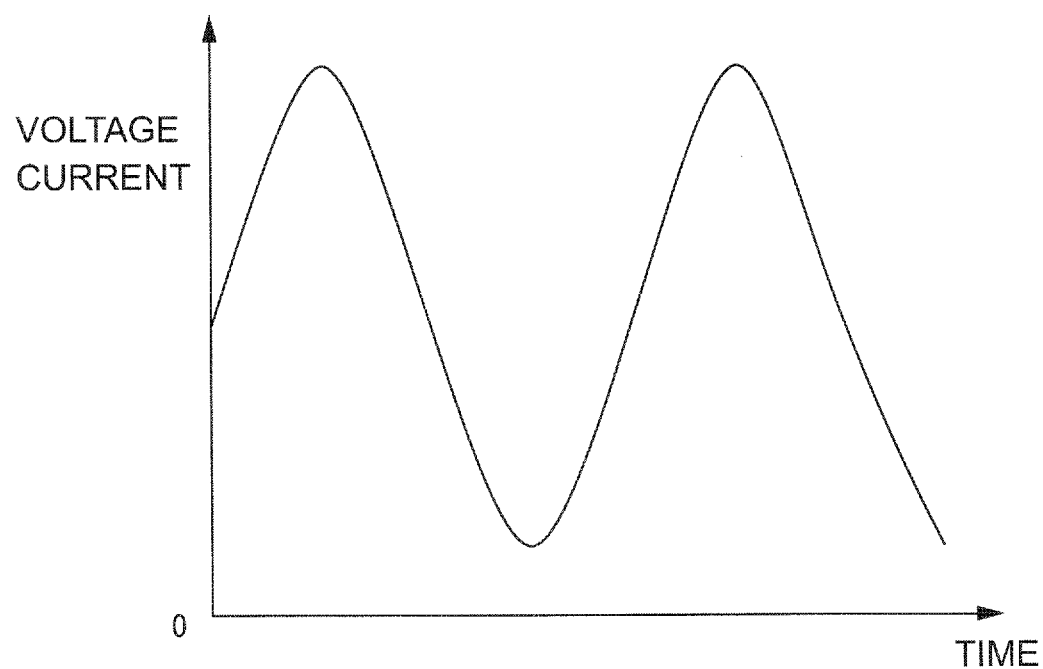

FIGS. 7A and 7B are conceptual diagrams illustrating a spatial modulator of this embodiment. In order to allow driving magnetic garnet films 48A constituting a spatial modulator 48 as illustrated in FIG. 7A by a voltage or current pixel by pixel, electrodes (not illustrated) are added, and this spatial modulator 48 is disposed at the position of the acoustic optical device 23 in FIG. 4. Then, by applying a voltage or current to each pixel of the magnetic garnet films 48A, the polarized surface of each pixel rotates by a magneto-optic effect, where the degree of this rotation of polarized surface is determined by the magnitude of the voltage or current to be applied. As the spatial modulator 48 having such a structure, there is one whose number of pixels is 128×128 and which has a response speed of 15 ns.

Moreover, the voltage or current is applied to each pixel in the shape illustrated in FIG. 7B in a direction perpendicular to the scanning direction of this spatial modulator 48 so that the intensity or phase of a light which passed through the polarized beam splitter 27 of FIG. 4 becomes a sine grating pattern in a strip form. At that time, by causing a single vibration at a frequency fm=±2πv/d which is displaced in phase in each pixel, this grating can be moved at a velocity v.

Specifically, when the pitch of this grating in a sine wave form is d, and a moving speed thereof is v, the following equation holds.

$$A \cos\{2\pi/d(x-vt)\} = A/2(\exp j\{2\pi/d(x-vt)\} + \exp j\{-2\pi/d(x-vt)\})$$

Accordingly, the positive and negative first order diffracted lights have a modulation frequency fm=±2πv/d. Note that in the case of intensity, a zero order direct current component is generated, but it does not affect the beat signal since it is a direct current component.

Here, the positive and negative first order diffracted lights are to the extent that the beams are overlapped in a desired degree by the pitch of the sine grating and the magnification of the pupil transmission magnifying lens system, similarly to Embodiment 2. Further, effects similar to those of Embodiment 2 can be obtained by determining the velocity v so that the modulation frequency fm becomes about 8 MHz. The response speed of the spatial modulator 48 is set to 15 ns, but the spatial modulator in the current situation is digital and binary.

However, it is possible to perform analog modulation, and the response speed at that time is to the extent that there is a possibility of deterioration by about one order of magnitude. By using it in combination with the pupil transmission magnifying lens system, it is possible to sufficiently obtain a modulation frequency equal to or more than 8 MHz. In this case, as compared to Embodiment 2, the pupil transmission magnifying lens system becomes simple. This is because, while the modulation frequency is determined by the response speed of the device, the degree of separation of the beams can be made small when the pitch of the grating is made as large as possible.

Therefore, the smallest degree of separation is determined by the size of the device, and thus high-speed scanning is possible by appropriately selecting the size. Note that also the driving circuit and the like can be simplified by making the pixels themselves of the above-described spatial modulator 48 in a strip form as illustrated in FIG. 7.

Note that when elements which cause a Raman-Nath diffraction are used also in the acoustic optical device 23, by denoting the modulation frequency by fm, the positive and negative first order diffracted lights can be made to have the modulation frequency fm from the following equation.

$$A \cos(2\pi f m t) = A/2(\exp(j2\pi f m t) + \exp(-j2\pi f m t))$$

In this case, similar effects can be achieved by a simpler modulation signal than that of modulation like the DSB modulation.

Hereinafter, Embodiment 5 to Embodiment 10 related to an optical resolution improvement apparatus according to the present invention will be described in detail based on the drawings.

Embodiment 5

Embodiment 5 of an optical resolution improvement apparatus according to the present invention will be described below with reference to FIG. 8.

Figure 8:
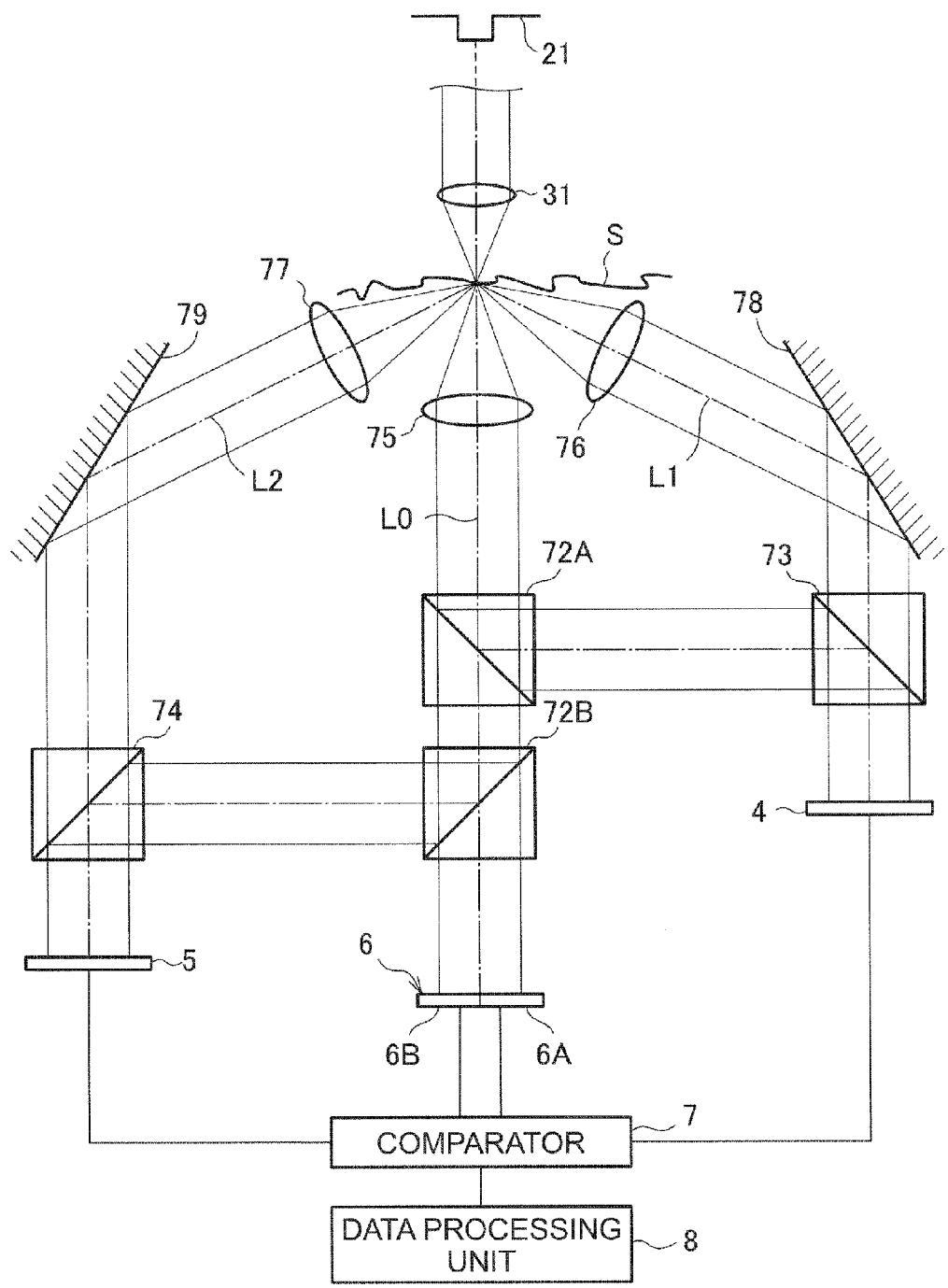
FIG. 8 is a schematic diagram representing an optical system illustrating Embodiment 5 related to an optical resolution improvement apparatus of the present invention.

FIG. 8 is a schematic diagram illustrating a structure of the optical resolution improvement apparatus of this embodiment. As illustrated in FIG. 8, a laser light source 21 which emits a light is disposed to oppose an objective lens 31 via a not-illustrated optical apparatus, and the light emitted by this laser light source 21 is converged and irradiated to a sample S as an is object under measurement which is a transmissive object. On an optical axis L0 which is an irradiation optical axis of the convergent irradiation of this laser light source 21, a lens 75 as a first lens which is a convex lens is positioned, and a luminous flux which is transmitted through the sample S as the object under measurement and emitted therefrom is converted by the lens 75 into a parallel luminous flux.

On the optical axis L0 below this lens 75, two first beam splitters 72A, 72B which divide the parallel luminous flux emitted from the lens 75 to the right and the left, respectively, are disposed sequentially, and a first photo detector 6 receiving this light is located below them. However, this first photo detector 6 is constituted of two divided photo detectors 6A, 6B located with the optical axis L0 being interposed therebetween. Then, the divided photo detector 6A on the right side receives a portion on the right side of the optical axis L0 in the transmitted light from the lens 75, and the divided photo detector 6B on the left side receives a portion on the left side of the optical axis L0 in the transmitted light from the lens 75.

On the other hand, on an optical axis L1 which is a tilted optical axis having a tilt on the right side of FIG. 8 with respect to the optical axis L0, a lens 76 as a second lens which is a convex lens is located, and this lens 76 converts the luminous flux emitted from the sample S into a parallel luminous flux. On this optical axis L1, a reflecting mirror 78 for reflecting the parallel luminous flux is disposed, and further below this reflecting mirror 78, a second beam splitter 73 is located. Accordingly, the reflecting mirror 78 disposed between the lens 76 and the second beam splitter 73 reflects the emitted lights from the lens 76 toward the second beam splitter 73 side. Further, below the second beam splitter 73, a second photo detector group 4 constituted of a plurality of divided photo detectors is located.

Moreover, the first beam splitter 72A on the upper side out of the two first beam splitters 72A, 72B sends the divided luminous flux toward the second beam splitter 73 side. Accordingly, the second beam splitter 73 makes the luminous flux emitted from the lens 75 and the luminous flux emitted from the lens 76 interfere with each other, and these luminous fluxes are received by the second photo detector group 4.

On the other hand, a lens 77, a reflecting mirror 79, a second beam splitter 74, and a second photo detector group 5 which have the same structures as described above are disposed on the left side of FIG. 8 symmetrically with respect to the optical axis L0. Thus, the two first beam splitters 72A, 72B and the right and left second beam splitters 73, 74 make the luminous flux emitted from the lens 75 and the luminous fluxes emitted from the lenses 76, 77 interfere with each other.

Moreover, the above-described divided photo detectors 6A, 6B and the photo detector groups 4, 5 are connected to a comparator 7 for comparing signals from the photo detectors 6A, 6B and the photo detector groups 4, 5. Then, this comparator 7 is connected to a data processing unit 8 which finally processes data to obtain the profile of the sample S, and the like. Accordingly, the comparator 7 and the data processing unit 8 constitute an output difference detection unit detecting an output difference between the divided photo detectors 6A, 6B of the first photo detector 6 located with the optical axis L0 being interposed therebetween and an output difference between the pair of second photo detector groups 4, 5.

From the above, the lights converged at the objective lens 31 illustrated in FIG. 8 forms a spot on the sample S as the object under measurement. This spot ideally has the diameter of the diffraction limit, and spatial frequency information of a pattern of the sample S inside this spot diameter is diffracted as a transmitted light. Here, when the spatial frequency of a light not incident on the lens 75 within the first order diffracted light of the spatial frequency which the sample S has is considered, the zero order diffracted light which is transmitted through the sample S and the light of a spatial frequency component lower than the aforementioned spatial frequency are incident on the lens 75. From this fact, with the lens 75 alone, the pattern of the sample S can be reproduced up to the cut-off frequency which the lens 75 has.

However, the spatial frequency of a light not incident on the lens 75 is cut, and this results in a defect of image information. Accordingly, the lens 76 and the lens 77 are disposed to have a certain tilt at positions symmetrical to each other with respect to the optical axis L0 of the zero order diffracted light, as illustrated in FIG. 8. Here, the tilt angles of the optical axes L1, L2 of the lens 76 and the lens 77 relative to the optical axis L0 of the zero order diffracted light are set to be comparable to the spatial frequency at which the contrast of the sample S becomes maximum.

Specifically, the luminous flux on the optical axis L1 of the lens 76 is returned by the reflecting mirror 78 and is combined by the beam splitter 73 with the luminous flux on the optical axis L0 of the zero order diffracted light separated by the beam splitter 72A. The combined light itself is guided to the photo detector group 4. Therefore, the zero order diffracted light and the first order diffracted light emitted from the lens 76 are made to interfere, and the photo detector group 4 receives these lights. This is because, at that time, the luminous flux having the highest contrast becomes the luminous flux of the spatial frequency matching the optical axis L1 of the lens 76.

When a similar optical system is considered, which is located in a direction opposite to the above-described optical system with respect to the optical axis L0 of the zero order diffracted light, the luminous flux on the optical axis L2 which is the tilted optical axis of the lens 77 is returned by the reflecting mirror 79. The luminous flux on the optical axis L2 of this lens 77 is combined by the beam splitter 74 with the luminous flux on the optical axis L0 of the zero order diffracted light passed through the beam splitter 72A and returned by the beam splitter 72B. The combined lights themselves are guided to the photo detector group 5. Therefore, the zero order diffracted light and the negative first order diffracted light emitted from the lens 77 are made to interfere, and the photo detector group 5 receives these lights.

Here, the photo detector group 4 is constituted of a plurality of divided photo detectors, and each divided photo detector obtains interference fringe intensity resulting from sampling, at appropriate pitches, interference fringes of interference of the zero order diffracted light and the first order diffracted light. Specifically, this is because when the optical axis L0 of the zero order diffracted light and the optical axis L1 of the first order diffracted light do not have a tilt, they result in even interference intensity in a luminous flux, but when they have a tilt of some degree, they result in interference fringes at even pitches. The pitches of the interference fringes are due to the emission angle of the first order diffracted light, and thus reflecting the spatial frequency which is incident on the lens 76.

Further, the photo detector group 5 is also constituted of a plurality of divided photo detectors, and each divided photo detector obtains interference fringe intensity resulting from sampling, at appropriate pitches, interference fringes of interference of the zero order diffracted light and the negative first order diffracted light, and operates in the same manner as above.

Therefore, the photo detector groups 4, 5 are disposed in the form that they are each constituted of a plurality of divided photo detectors, and information reflected by the spatial frequency can be obtained. By obtaining an output difference between the divided photo detectors which obtain substantially corresponding spatial frequencies in the photo detector groups 4, 5, higher spatial frequency information can be obtained.

The above is effective particularly in an optical system of the DPC method and an optical system combining the DPC method and the heterodyne method, which is proposed by the present inventors. For simplicity, it is described with the transmissive optical system above, but disposing this optical resolution improvement apparatus in a direction reflecting from a sample surface provides similar effects.

The point that the substantial spatial frequency which can be obtained by the above optical system can be increased is clarified quantitatively below. However, for simplicity of explanation, the sample S is assumed to be in the form of a sine wave with a height h and a pitch d. Specifically, an optical phase θ is represented by the following equation.

$$\theta = 2\pi h/\lambda \sin(2\pi x/d + \theta 0)$$ Equation (9)

The amplitude E of a light deflected from the sample S is given as a convolution of Fourier transform of Equation (9) and the aperture of the lens on a plane separated by the focal length f, and hence is represented as follows. However, the Bessel function which is Fourier transform of the phase of Equation (9) takes up to the positive and negative first order. Here, $E_0$ and $E_1$ are complex amplitude distributions of the zero order diffracted light and the first order diffracted light, respectively, passing through the lens 75 and the lens 76 on which they are incident. They are represented by Equations (10) and (11), respectively.

$$E_0 = \int J_0\left(2\pi\frac{h}{\lambda}\right)\delta(X)rect\left(\frac{x-X}{2a}\right)dX = J_0\left(2\pi\frac{h}{\lambda}\right)rect\left(\frac{x}{2a}\right)$$ Equation (10)

$$E_1 = \int J_1\left(2\pi\frac{h}{\lambda}\right)(j\sin\theta_0 - \cos\theta_0)\delta\left(X - \frac{\lambda f}{d}\right)rect\left(\frac{x-X}{2a}\right)dX$$

$$= J_1\left(2\pi\frac{h}{\lambda}\right)(j\sin\theta_0 - \cos\theta_0)rect\left(\frac{x - \frac{\lambda f}{d}}{2a}\right)$$ Equation (11)

Similarly, when is a complex amplitude distribution which is an amplitude distribution of the negative first order diffracted light passing through the lens 77 on which it is incident, it is as following Equation (12).

Equation (12)

$$E_{-1} = \int J_1\left(2\pi\frac{h}{\lambda}\right)(j\sin\theta_0 + \cos\theta_0)\delta\left(X + \frac{\lambda f}{d}\right)rect\left(\frac{x-X}{2a}\right)dX$$

$$= J_1\left(2\pi\frac{h}{\lambda}\right)(j\sin\theta_0 + \cos\theta_0)rect\left(\frac{x + \frac{\lambda f}{d}}{2a}\right)$$

From Equation (10) representing the complex amplitude distribution of the zero order diffracted light and Equation (11) representing the complex amplitude distribution of the first order diffracted light, the intensity $I_1$ on the photo detector group 4 is as the following equation, which is a result of combining the luminous flux of the lens 75 and the luminous flux of the lens 76 by the beam splitters 72A, 73 and making them interfere with each other on the photo detector group 4.

$$I_1 = \left(J_0\left(2\pi\frac{h}{\lambda}\right) - J_1\left(2\pi\frac{h}{\lambda}\right)\exp(-j\theta_0)\right)^2$$

Similarly, from Equation (10) representing the complex amplitude distribution of the zero order diffracted light and Equation (12) representing the complex amplitude distribution of the negative first order diffracted light, the intensity $I_2$ on the photo detector group 5 is as the following equation, which is a result of combining the luminous flux of the lens 75 and the luminous flux of the lens 77 by the beam splitters 74, 72B and making them interfere with each other on the photo detector group 5.

$$I_2 = \left(J_0\left(2\pi\frac{h}{\lambda}\right) + J_1\left(2\pi\frac{h}{\lambda}\right)\exp(-j\theta_0)\right)^2$$

However, for simplicity, the intensity $I_1$ and the intensity $I_2$ are ones such that there is substantially no optical path difference between the zero order diffracted light and the positive and negative first order diffracted lights. When the difference output of the photo detector group 4 and the is photo detector group 5 is represented in this manner, it is as following equation.

$$\Delta I = I_1 - I_2 \propto -4 J_0\left(2\pi\frac{h}{\lambda}\right) J_1\left(2\pi\frac{h}{\lambda}\right)\cos\theta_0$$

Here, the reason for using the photo detector groups each constituted of an appropriate number of divided photo detectors instead of using a sole photo detector is that they enables an analysis also considering the distribution of the spatial frequency component included in the sample S from the amount of received light because the photo detector and the spatial frequency are in a correspondence.

If the zero order diffracted light and the first order diffracted light are not made to interfere, the intensity of the positive and negative first order diffracted lights is as the following equation, and when the difference output is obtained, it becomes 0.

$$I = E_1^2$$
$$= E_{-1}^2 \propto \left(J_1\left(2\pi\frac{h}{\lambda}\right)\right)^2$$

Further, if an output of summation is obtained, the phase information $\theta_0$ is completely lost. The result is only information about whether the spatial frequency exists or not in the sample S, and information desired to be known such as profile information cannot be obtained.

The optical system of the DPC method and the optical system combining the DPC method and the heterodyne method, to which it is effective to specifically apply the above-described optical system, will be described below. Here, FIG. 9 illustrates a block diagram of a transmissive optical system in the DPC method, and FIG. 10 illustrates a block diagram of a reflective optical system in the DPC method.

Figure 9:
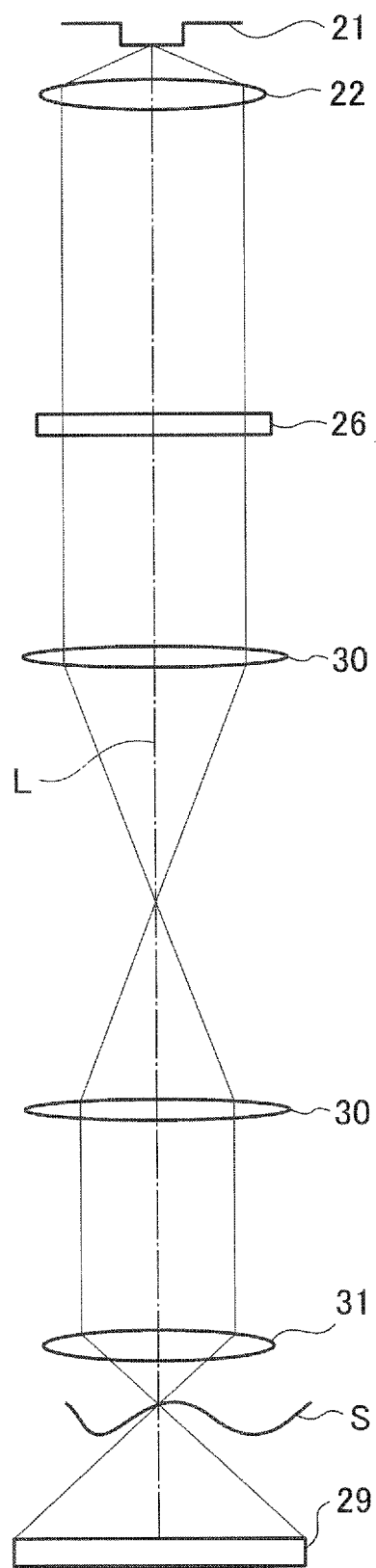
FIG. 9 is a block diagram representing a transmissive optical system in a DPC method.
Figure 10:
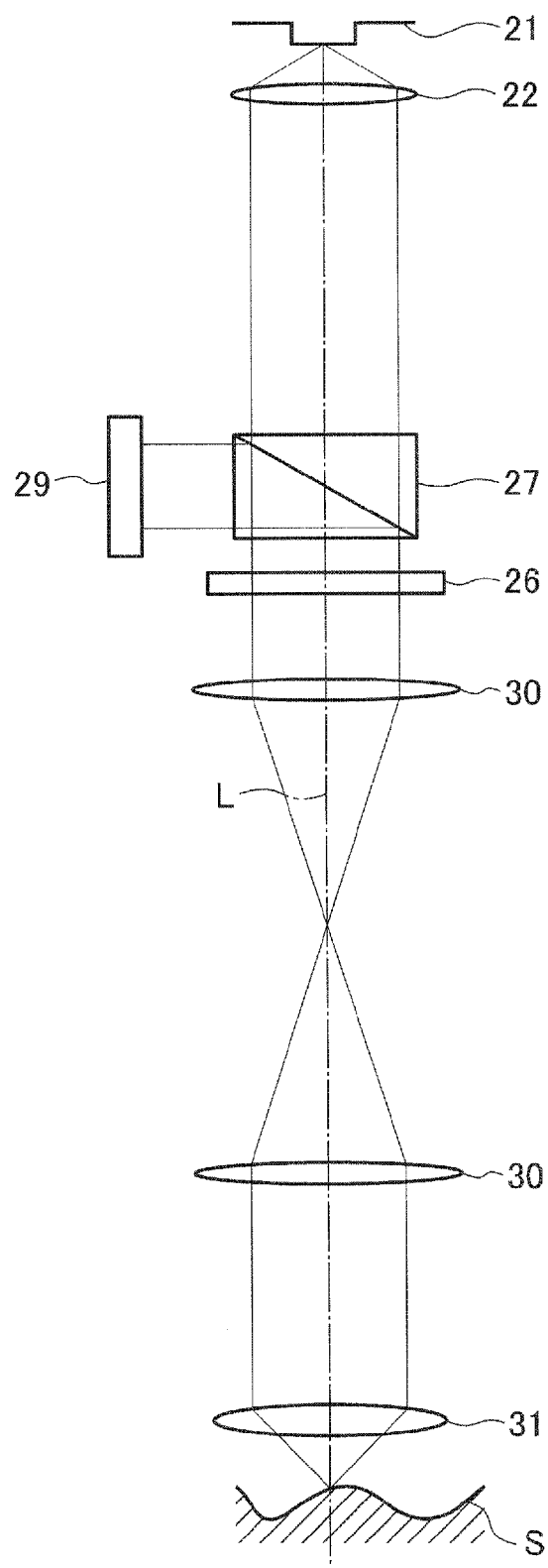
FIG. 10 is a block diagram representing a reflective optical system in the DPC method.

First, as illustrated in FIG. 9, the luminous flux from the laser light source 21 is converted into a parallel luminous flux by the collimator lens 22 and is made to be incident on the two-dimensional scanning device 26. This two-dimensional scanning device 26 is a device which scans a light on a surface and is constituted of a MEMS, a galvano mirror, a resonant mirror, or the like.

This parallel luminous flux passes through the pupil transmission lens system 30 for transmitting the pupil position of the two-dimensional scanning device 26 to the pupil position of the objective lens 31 and is incident on the objective lens 31, and thereafter is converged on the sample S. The light converged on the sample S becomes a transmitted light and is incident on the photo detector 29. This photo detector 29 is a photo detector disposed at a position substantially in a far field from the sample S, and divided at least in two symmetrically with respect to the optical axis L.

As a result, the parallel luminous flux on the optical axis L is separated into the zero order diffracted light and the positive and negative first order diffracted lights by a refractive index distribution as well as convexes and concaves of the sample S, and these separated lights are received by the photo detector 29 while interfering with each other. Accompanying this, information of the refractive index distribution and the convexes and concaves of the sample S are converted in the not-illustrated photoelectric conversion unit in the photo detector 29 based on interference information of the zero order diffracted light and the positive and negative first order diffracted lights. At that time, the aforementioned information of the sample S is reflected on the difference output between the two photo detectors of the photo detector 29, which are symmetrical with respect to the optical axis L.

On the other hand, FIG. 10 is a block diagram of the reflective optical system, which is different from the transmissive optical system of FIG. 9 in that a beam splitter 27 is disposed between the collimator lens 22 and the two-dimensional scanning device 26. It is also different in that part of the luminous flux is taken out by the beam splitter 27, and this luminous flux is received by the photo detector 29 constituted of photo detectors divided at least in two, so as to detect an output difference between them. At that time, the reflected parallel light from the sample S is substantially far field information.

The above-described structures illustrated in FIG. 4 and FIG. 6 representing the embodiments related to the distance measurement system are also the optical system combining the DPC method and the heterodyne method, which is proposed by the present inventors. Here, FIG. 4 is also a block diagram of the reflective optical system combining the DPC method and the heterodyne method, and FIG. 6 is also a block diagram of the transmissive optical system combining the DPC method and the heterodyne method.

For this reason, a detailed explanation of the optical systems combining the DPC method and the heterodyne method is omitted. However, these optical systems differ from the optical systems illustrated in FIG. 9 and FIG. 10 in that, as illustrated in FIG. 4 and FIG. 6, two quite close luminous fluxes are generated by the acoustic optical device 23 and are irradiated to the sample S which is the object under measurement.

Further, by using the optical system illustrated in FIG. 8 for the photo detector part of the optical systems as above, it is possible to largely improve information with a higher spatial frequency, that is, a lateral resolution. Moreover, it is also possible to be an optical resolution improvement apparatus for a parallel luminous flux system by making the luminous flux irradiated to the sample S be a parallel luminous flux, omitting the lenses 75, 76, 77 illustrated in FIG. 8, and structuring the other optical system to be the same as the above embodiment.

Photo detector systems of the following embodiments may be applied to the photo detector part of the optical system of the DPC method and the photo detector part of the optical system combining the DPC method and the heterodyne method, and thus the explanation of optical systems other than the photo detector systems will be omitted in the following embodiments.

Embodiment 6

In this embodiment, a lens is installed to be tilted with respect to the optical axis L0 of the zero order diffracted light. Thus, it is possible to take in not only part of the zero order diffracted light but also part of the first order diffracted light having a higher spatial frequency compared to the case of using the same lens, realizing interference of these zero order diffracted light and first order diffracted light.

Figure 11:
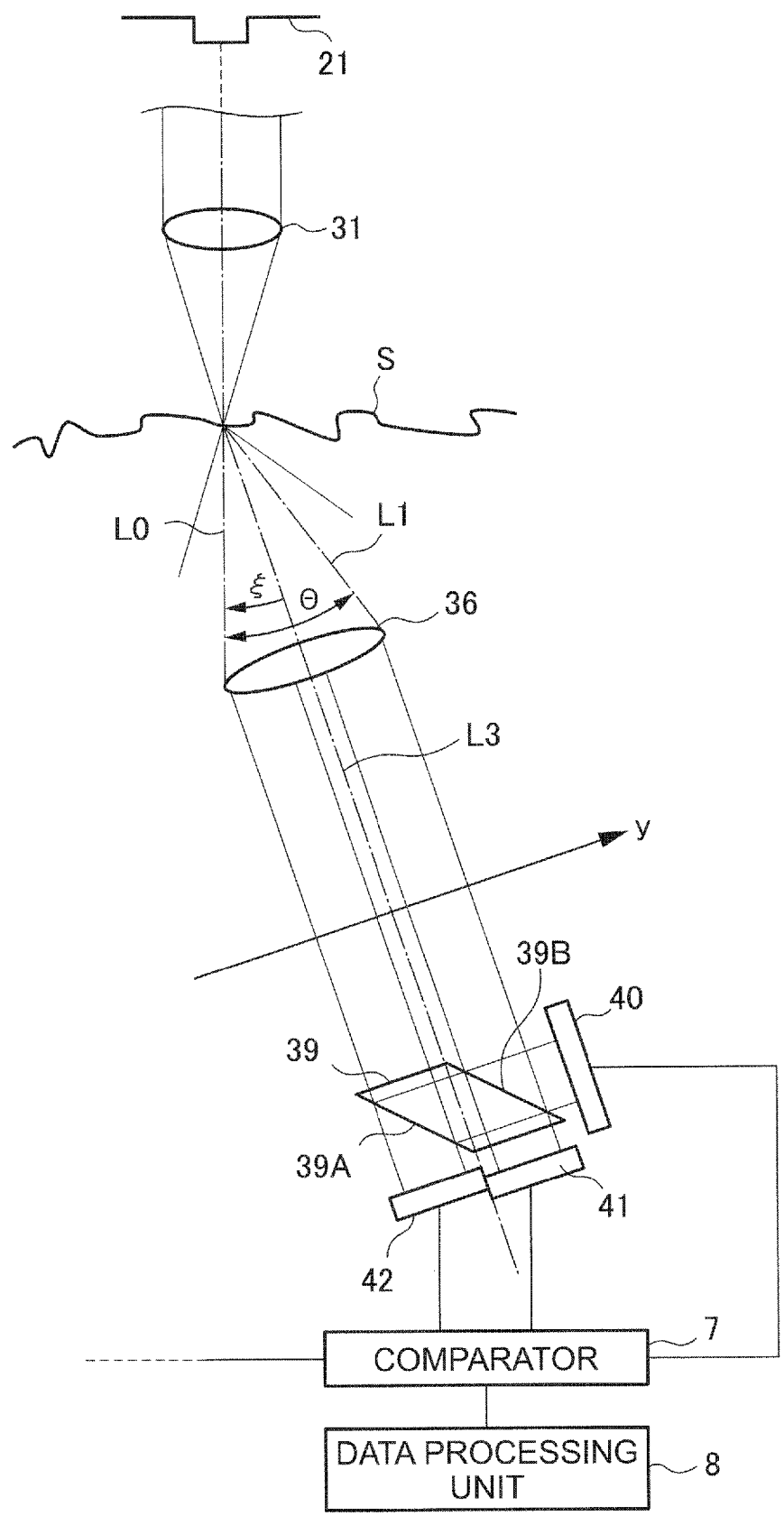
FIG. 11 is a schematic diagram representing an optical system illustrating Embodiment 6 related to the optical resolution improvement apparatus of the present invention.

As illustrated in FIG. 11, this embodiment is the same as in FIG. 8 up to that the parallel light is incident on the objective lens 31 and is converged on the sample S. However, in this embodiment, part of the zero order diffracted light and part of the first order diffracted light which are transmitted through the sample S are taken into a lens 36 in a state of being tilted by an optical axis L3 having an intermediate tilt angle between the zero order diffracted light and the first order diffracted light. Then, by shifting and overlapping the luminous fluxes of the partial first order diffracted light and the partial zero order diffracted light with each other by a rhomboid prism 39 or the like, their luminous fluxes are made to interfere with each other.

Further, one face of the rhomboid prism 39 is a translucent mirror 39A, the opposite face of this translucent mirror 39A is a translucent mirror 39B, and photo detectors 40, 41, 42 are disposed to receive lights which passed through the respective faces. Here, the photo detector 40 and the photo detector 41 each reflect a result of interference between the part of the zero order diffracted light and the part of the first order diffracted light. The photo detector 42 reflects a result of interference between the first order diffracted light of a low spatial frequency diffracted in an area including the part of the zero order diffracted light of the lens 36 and the part of the zero order diffracted light.

The results of interference of the zero order diffracted light and the first order diffracted light will be described with the following equations.

First, an optical system similar to the optical system illustrated in FIG. 11 is disposed also for the negative first order diffracted light to be symmetrical to the optical axis L0 of the zero order diffracted light, which is not illustrated in FIG. 11. When the difference output of these corresponding photo detectors is obtained, the following can be considered. For simplicity of explanation, when the sample S is assumed to be in the form of a sine wave with a height h and a pitch d, an optical phase θ is represented by the following equation.

$$\theta = 2\pi h/\lambda \sin(2\pi x/d + \theta 0)$$   Equation (9)

The amplitude E of a light deflected from the sample S is given as a convolution of Fourier transform of Equation (9) and the aperture of the lens on a plane separated by the focal length f, and hence is represented as follows.

However, the Bessel function which is Fourier transform of the phase of Equation (9) takes up to the positive and negative first order.

Further, as illustrated in FIG. 11, the optical axis L3 is tilted by an angle ξ substantially corresponding to $\sin^{-1}$ (NA) of the lens 36. At that time, a direction perpendicular to the optical axis L3 is y axis, and the center position of the first order diffracted light corresponding to the spatial frequency 1/d of Equation (1) is Y1.

At that time, when the optical axis L3 is tilted by the angle with reference to above Equation (2), the center of the zero order diffracted light of Equation (2) is displaced by a, and the center axis of the first order diffracted light becomes y1. Thus, a complex amplitude distribution $E_1$ is given by following Equation (13).

$$E_1 = J_0\left(2\pi\frac{h}{\lambda}\right)rect\left(\frac{y-a}{2a}\right) - J_1\left(2\pi\frac{h}{\lambda}\right)\left(rect\left(\frac{y-y1}{2a}\right)eyp(-j\theta_0)\right)$$   Equation (13)

Similarly, for the negative first order diffracted light in the optical system symmetrical to the first order diffracted light with respect to the optical axis L0 of the zero order diffracted light, it is as following Equation (14).

$$E_{-1} = J_0\left(2\pi\frac{h}{\lambda}\right)rect\left(\frac{y+a}{2a}\right) + J_1\left(2\pi\frac{h}{\lambda}\right)\left(rect\left(\frac{y-y1}{2a}\right)eyp(-j\theta_0)\right)$$   Equation (14)

Here, y1 is f tan(Θ−ξ).
Since $$\tan(\Theta) = \lambda/d$$

and $$\tan(\xi) = a/f = NA,$$

y1 is as the following equation.

$$y1 = f\frac{\frac{\lambda}{d} - \frac{a}{f}}{1 + \frac{\lambda a}{df}}$$

In the optical system of FIG. 11, the optical axis L3 of the lens 36 is substantially shifted and overlapped on the boundary between the zero order diffracted light and the first order diffracted light, and thus Equation (13) becomes following Equation (13)′.

$$E_1 = J_0\left(2\pi\frac{h}{\lambda}\right)rect\left(\frac{y}{2a}\right) - J_1\left(2\pi\frac{h}{\lambda}\right)\left(rect\left(\frac{y-y1}{2a}\right)eyp(-j\theta_0)\right)$$   Equation (13)′

Here, 0≤y≤a.
Equation (13)′ is $$E_1 = J_0\left(2\pi\frac{h}{\lambda}\right) - J_1\left(2\pi\frac{h}{\lambda}\right)eyp(-j\theta_0)$$

Here, y1−a≤y≤a.

Thus, the complex amplitude distribution $E_1$ is largest when y1=a, and is zero when y1=2a.

y1=2a means that information up to the spatial frequency equivalent to 3a is obtained when seen from the zero order diffracted light. Therefore, as compared to when the same lens of NA is used, a spatial frequency up to 1.5 times can be obtained. By this amount, the optical resolution is substantially improved.

On the other hand, for the negative first order diffracted light in the optical system symmetrical to the first order diffracted light with respect to the optical axis L0 of the zero order diffracted light, when a direction perpendicular to the optical axis L2 of the negative first order diffracted light is likewise y' axis, it is as following Equation (14)'.

$$E_{-1} = J_0\left(2\pi\frac{h}{\lambda}\right) rect\left(\frac{y'}{2a}\right) + J_1\left(2\pi\frac{h}{\lambda}\right)\left(rect\left(\frac{y-y1}{2a}\right) eyp(j\theta_0)\right) \quad \text{Equation (14)'}$$

Here, $0 \leq y \leq a$.
Equation (14)' is $$E_{-1} = J_0\left(2\pi\frac{h}{\lambda}\right) + J_1\left(2\pi\frac{h}{\lambda}\right) eyp(j\theta_0)$$

Here, $-a \leq y' \leq y1+a$.

Thus, the complex amplitude distribution $E_{-1}$ is largest when $y1=-a$, and is zero when $y1=-2a$.

$y1=-2a$ means that information up to the spatial frequency equivalent to $-3a$ is obtained when seen from the zero order diffracted light. Therefore, as compared to when the same lens of NA is used, a spatial is frequency up to 1.5 times can be obtained. It is similar to the first order diffracted light in that, by this amount, the optical resolution is substantially improved.

For the information obtained in this manner, a difference output $\Delta I$ between a summation output of the photo detector 40 and the photo detector 41 and the photo detector of the negative first order diffracted light equivalent thereto is obtained by the following equation.

$$\Delta I = E_1^2 - E_{-1}^2 \propto -4J_0\left(2\pi\frac{h}{\lambda}\right) J_1\left(2\pi\frac{h}{\lambda}\right) \cos\theta_0$$

This is substantially the same equation as that in Embodiment 5. However, the optical system is simpler compared to Embodiment 5 and is constituted of a simple element like the rhomboid prism, and shaping the lens integrally, or the like enables to make a stable optical system. Note that similar effects can be provided by the rhomboid prism substantially constituted of two half mirrors.

Embodiment 7

Embodiment 7 of an optical resolution improvement apparatus according to the present invention will be described below with reference to FIG. 12.

Figure 12:
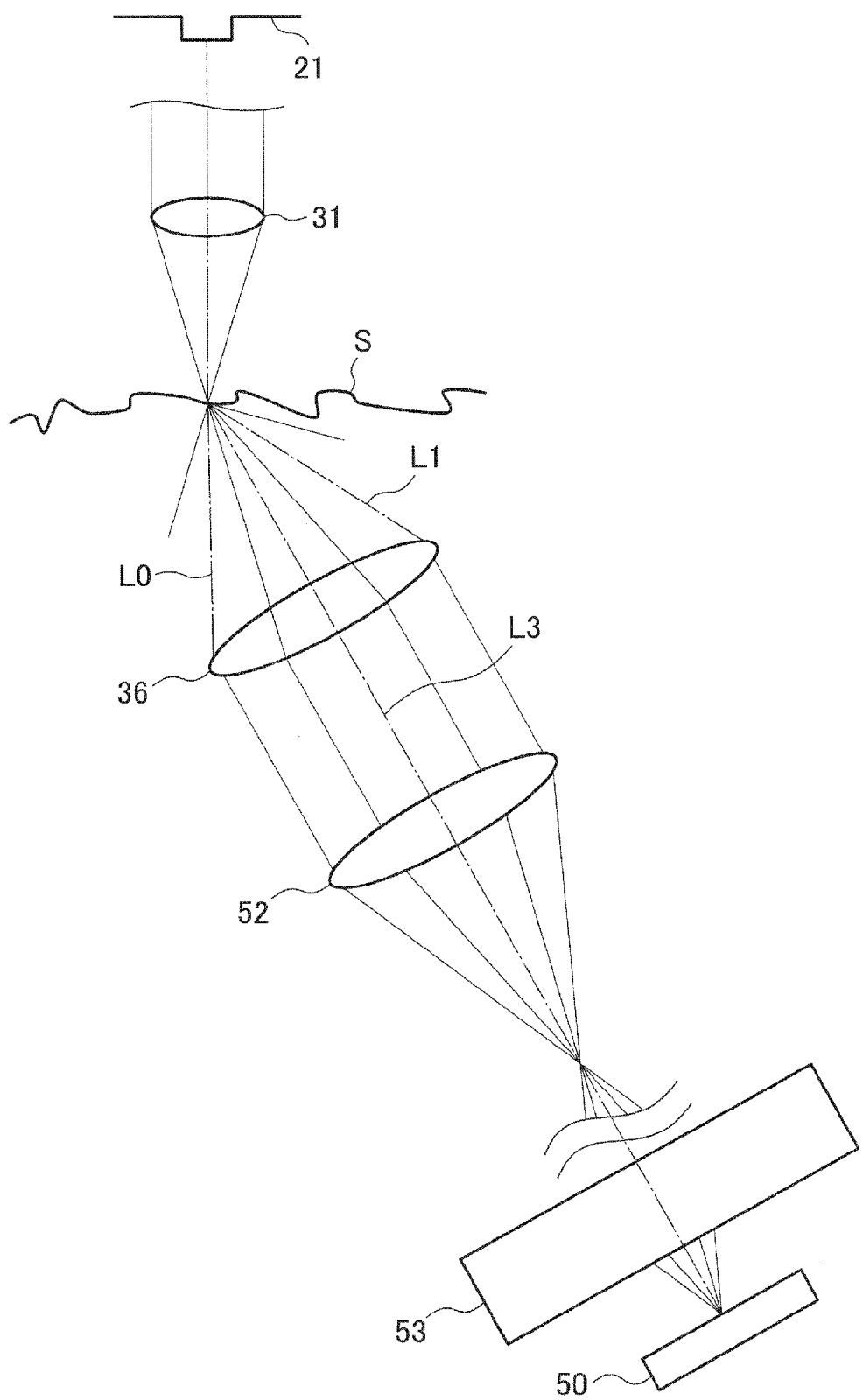
FIG. 12 is a schematic diagram representing an optical system illustrating Embodiment 7 related to the optical resolution improvement apparatus of the present invention.

FIG. 12 is a schematic diagram illustrating a structure of the optical resolution improvement apparatus of this embodiment. As illustrated in FIG. 12, in this embodiment, a lens 36 is installed to be tilted with respect to the optical axis L0 of the zero order diffracted light. Because of this, not only part of the zero order diffracted light but also part of the first order diffracted light having a higher spatial frequency compared to the case of using the same lens are taken in, realizing interference in an imaging optical system. Note that, although not illustrated, an identical optical system is disposed at a symmetrical position with respect to the axis L0 in this embodiment.

This embodiment is the same as the Embodiment 6 up to that the lens 36 is tilted and part of the zero order diffracted light and part of the first order diffracted light are obtained. In this embodiment, the diffracted lights which are converted into a parallel luminous flux by the lens 36 are gathered in the lens 52. The diffracted lights are overlapped with each other by this lens 52 in the vicinity of a focal point and substantially interfere. However, it is not interfere of the zero order diffracted light and the positive and negative first order diffracted lights, and thus it is different from imaging of the sample S itself.

Moreover, the pitches of interference fringes can be widened by elongating the effective focal length of the lens 52. If the focal lengths of the lens 36 and the lens 52 are the same, the pitches are naturally the same, and become the spatial frequency of the sample S. On the other hand, interference made by the other optical system of the negative first order diffracted light results in interference fringes with shifted pitches. However, when the photo detectors are large with respect to the pitches of the interference fringes, positioning of the elements receiving the positive and negative first order diffracted lights is difficult.

Accordingly, when the interference fringes themselves are enlarged by a magnifying optical system 53 and are made substantially equal to the size of a photo detector 50, inverse phases naturally occurs in the positive and negative first order diffracted lights, and thus the darkness and brightness reverse in the form that the zero order diffracted light becomes a bias. In this manner, information can be obtained quite easily up to an area where the spatial frequency is high. In the case of this embodiment, since the lens 52 is used, a wavefront aberration is tolerated to the extent that the phase difference between the zero order diffracted light and the first order diffracted light which are incident on this lens 52 is reflected as it is. Therefore, it is not necessary to use an expensive lens.

Note that in this embodiment, even lenses having focal lengths which are different in some degree can be used as they are because they are to the extent that the pitches of interference fringes change in some degree if there is no large change in amount of light to be received in the photo detectors for them and the wavefront aberration in the lens surface is not large. Further, the limit of the spatial frequency which can be obtained is about 1.5 times because the principle is substantially the same as in FIG. 11. This optical system is constituted by using only the lens system and thus is very simple and strong against disturbances.

Embodiment 8

Embodiment 8 of an optical resolution improvement apparatus according to the present invention will be described below with reference to FIG. 13.

Figure 13:
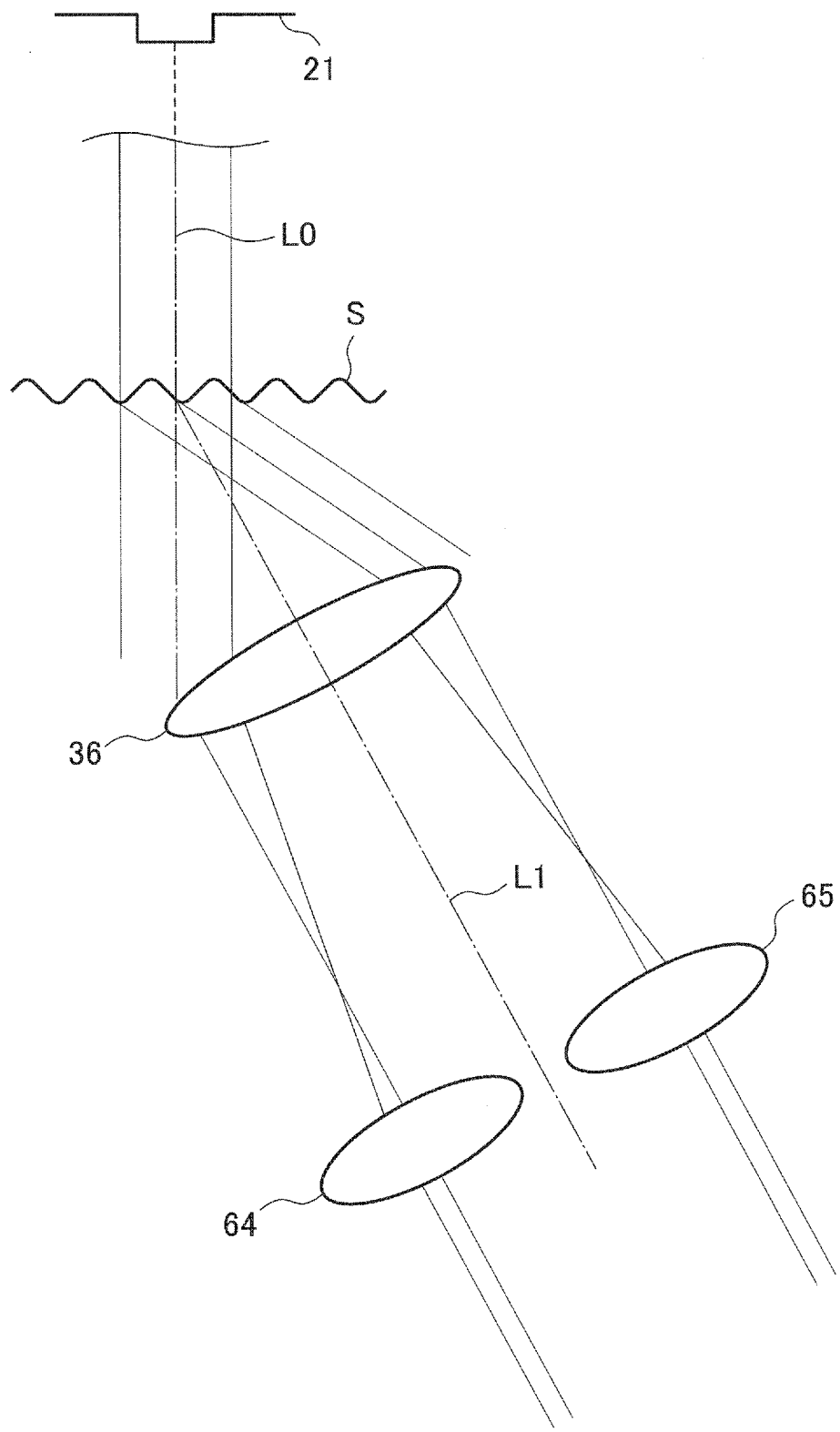
FIG. 13 is a schematic diagram representing an optical system illustrating Embodiment 8 related to the optical resolution improvement apparatus of the present invention.

FIG. 13 is a schematic diagram illustrating a structure of the optical resolution improvement apparatus of this embodiment.

As illustrated in FIG. 13, in this embodiment, a converged light is not incident on the sample S, but a parallel luminous flux having a relatively large diameter is incident thereon. In this case, a lens 36 is installed to be tilted with respect to the optical axis L0 of the zero order diffracted light. Because of this, not only part of the zero order diffracted light but also part of the first order diffracted light having a higher spatial frequency compared to the case of using the same lens can be taken in. Note that, although not illustrated, an identical optical system is disposed at a symmetrical position with respect to the axis L0 in this embodiment.

However, this embodiment is the same as the Embodiment 6 up to that the lens 36 is tilted and part of the zero order diffracted light and part of the first order diffracted light are obtained. In this embodiment, the zero order diffracted light and the first order diffracted light are both a condensed luminous flux. Separate lenses 64, 65 having focal points at respective focal positions of the lens 36 are disposed, and the condensed luminous flux is converted into a parallel luminous flux by these lenses 64, 65. After the conversion into a parallel luminous flux in this manner, the part of the zero order diffracted light and the part of the first order diffracted light are made to interfere with each other by using the optical systems illustrated in FIG. 11 and FIG. 12.

In this case, the diameter of the luminous flux to be incident on the sample S is large, and thus information in the plane is averaged. Accordingly, by providing a not-illustrated limit aperture for the incident parallel luminous flux, the information is construed as the information of this portion, or it becomes possible to detect an irregular pattern in a regular pattern. Specifically, since the direction of a regular first order diffracted light is known in advance from the design, the direction of the first order diffracted light can be suppressed by masking the focal point of the lens 36.

On the other hand, the other components will be incident on the lenses 64, 65, and thus information from a defect portion can be detected. For example, an application to defect inspection on a semiconductor wafer, inspection of unevenness in a nano-structure, or the like is possible. Note that the limit of the spatial frequency which can be obtained is about 1.5 times because the principle is substantially the same as in FIG. 11.

Embodiment 9

Embodiment 9 of an optical resolution improvement apparatus according to the present invention will be described below with reference to FIG. 14.

Figure 14:
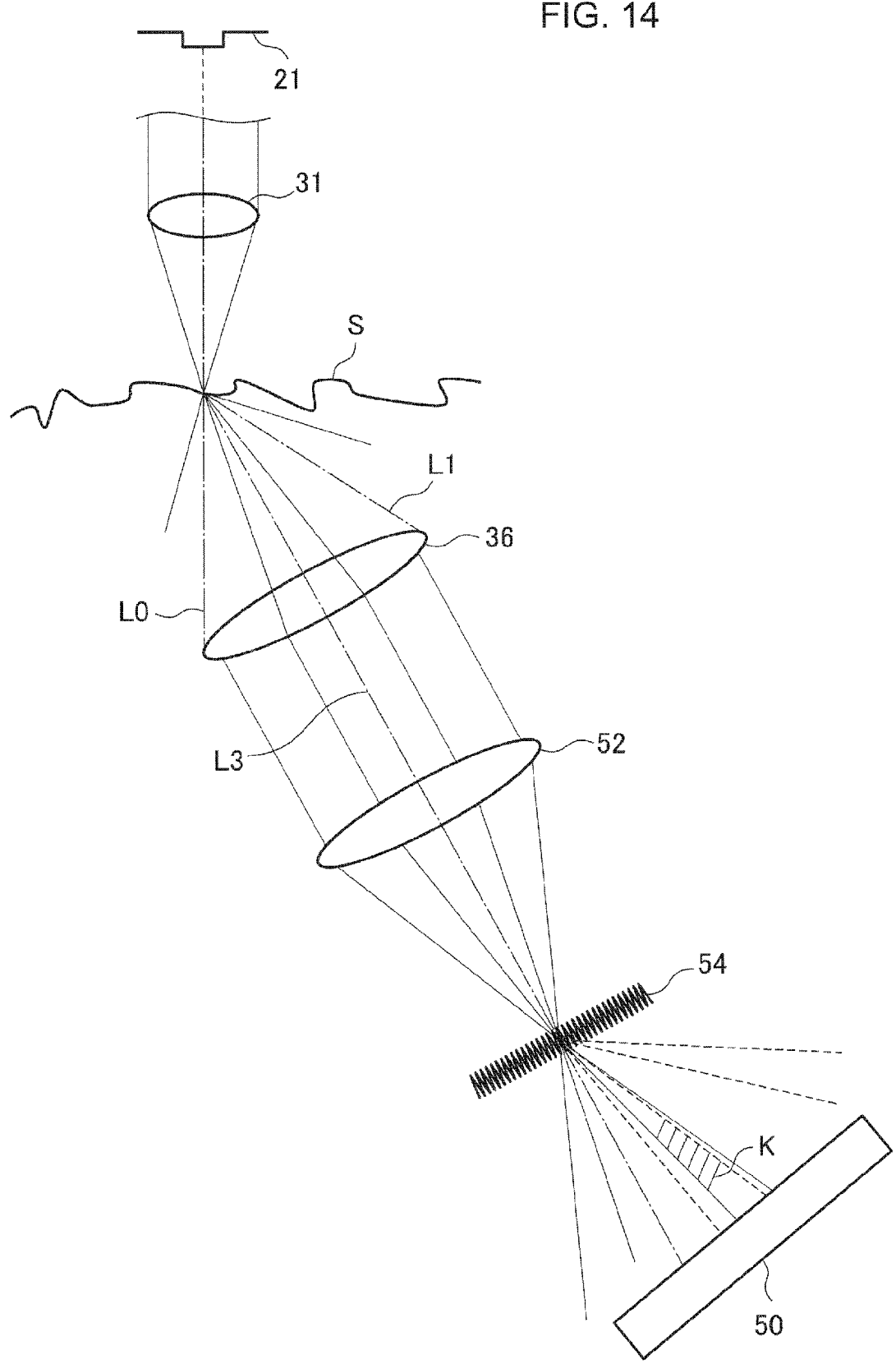
FIG. 14 is a schematic diagram representing an optical system illustrating Embodiment 9 related to the optical resolution improvement apparatus of the present invention.

FIG. 14 is a schematic diagram illustrating a structure of the optical resolution improvement apparatus of this embodiment. This embodiment is employed for an optical system similar to FIG. 12. This embodiment has a structure in which, as illustrated in FIG. 14, a grating 54 as a diffraction grating is disposed at a focal point of the lens 52 instead of the magnifying optical system 53 being deleted. Note that, although not illustrated, an identical optical system is disposed at a symmetrical position with respect to the optical axis L0 in this embodiment.

As a result, the zero order diffracted light and the first order diffracted light which are diffracted by the sample S are further diffracted by the grating 54, and the zero order diffracted light and the first order diffracted light substantially interfere with each other. In FIG. 14, the hatched part is an interference part K where the zero order diffracted light and the first order diffracted light overlap, and a similar interference part K exists also on the opposite side for the optical axis L3.

Here, when the grating 54 is constituted to have a sine wave form, diffracted waves by the grating 54 do not have a phase difference in the zero order diffracted light and the positive and negative first order diffracted lights. In this case, the phase difference in portions symmetrical to the optical axis L3 is the same, and thus the overlapped portions are in the same phase. Therefore, in this embodiment, the photo detector 50 may obtain the light amounts of the portions including the interference parts K of at least two areas outputted from the grating 54.

However, although the interference parts K are symmetrical and in the same phase with respect to the optical axis L0, for the negative first order diffracted light diffracted by the sample S, the phase of the interference part K reverses by 180 degrees. On the other hand, the intensity of part other than the interference part K is the same in the direction of the positive and negative first order diffracted lights which are diffracted by the sample S, and thus when a differential output of the intensity of the positive and negative first order diffracted lights is taken, information of only the interference part K remains.

On the other hand, when the grating 54 is constituted of a substantial sine wave shape which generates a phase difference, there occurs a phase difference of 180° between the zero order diffracted light and the positive and negative first order diffracted lights by the grating 54. In this case, as described above, the photo detector 50 may obtain the light amount of the portion including the interference part K of at least one area outputted from the grating 54, as described above. However, the point different from the above is that the phase difference which the grating 54 has is reflected here, and thus the position with respect to the beams of the grating 54 is also reflected. Therefore, position adjustment with respect to the beams of the grating 54 is necessary.

Note that the position adjustment is very easy. For the sample S prepared in advance, which has a phase grating having a certain spatial frequency, the adjustment may be performed so that the intensity modulation of the photo detector 50 on the both sides observed by scanning becomes maximum, and the phase difference becomes 180° on the both sides. The point that information of only the interference part K remains when the differential output of the intensity of the positive and negative first order diffracted lights is taken is the same as above.

Embodiment 10

Embodiment 10 of an optical resolution improvement apparatus according to the present invention will be described below with reference to FIG. 15.

Figure 15:
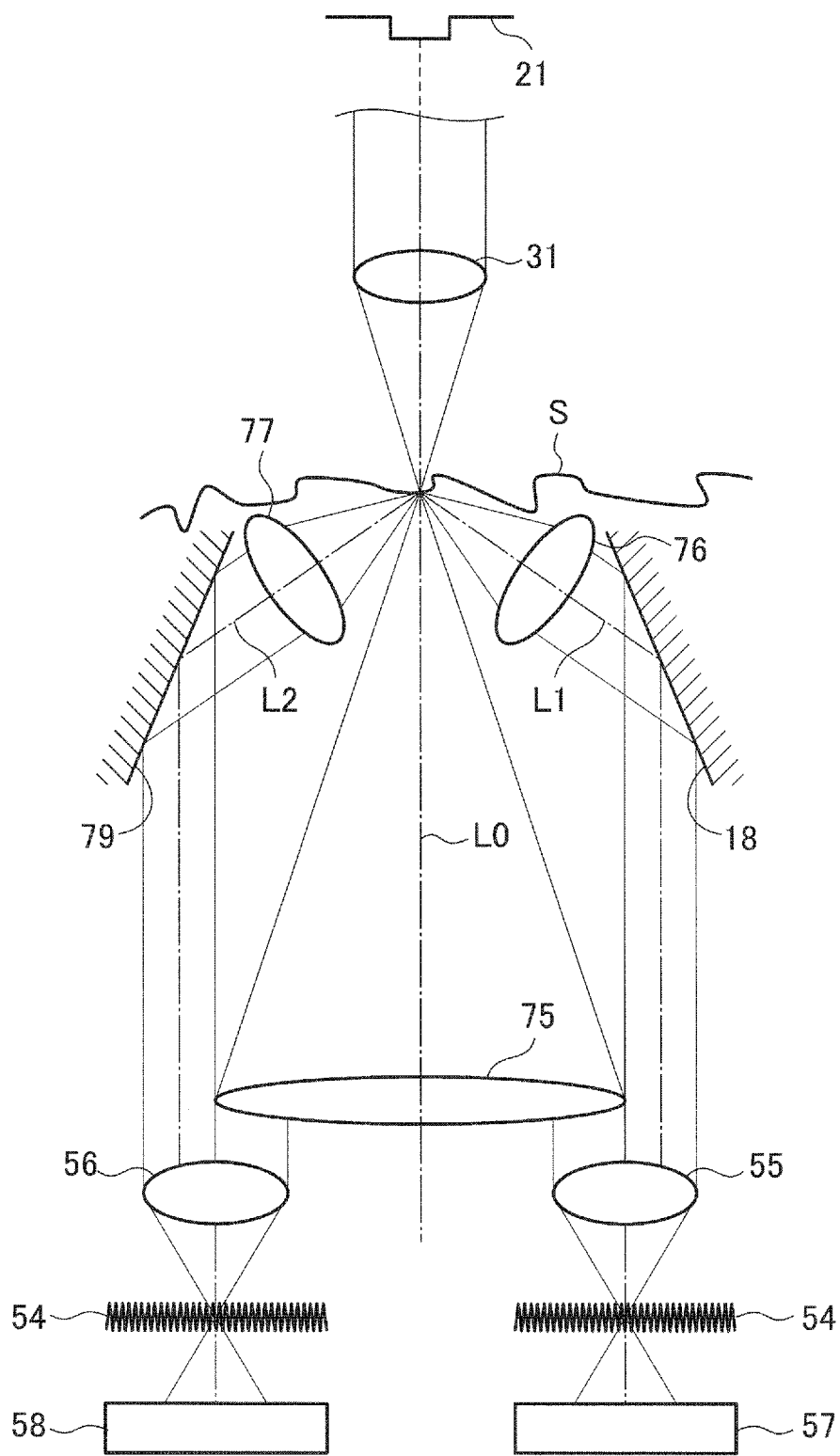
FIG. 15 is a schematic diagram representing an optical system illustrating Embodiment 10 related to the optical resolution improvement apparatus of the present invention.
Figure 16:
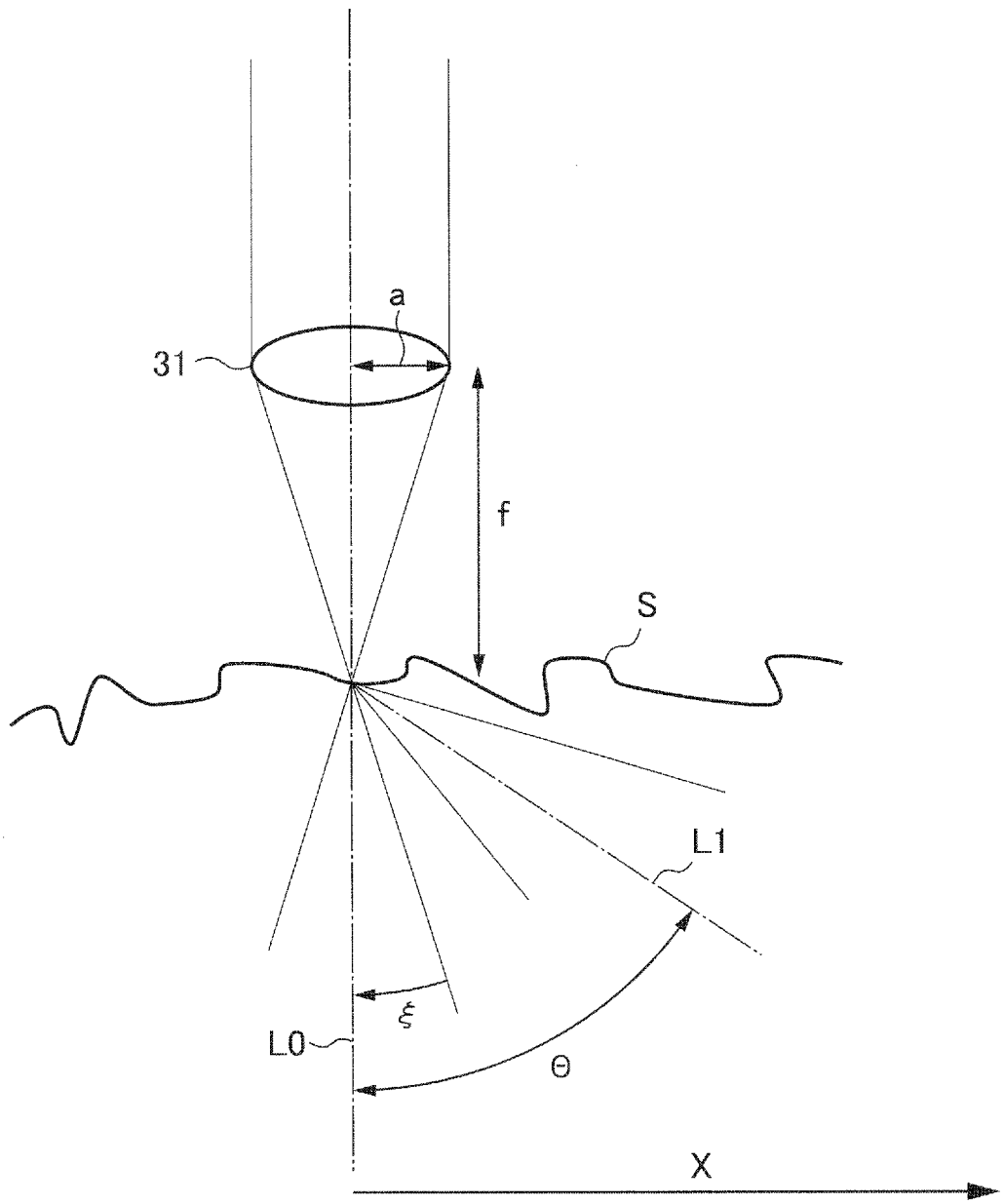
FIG. 16 is a principle diagram explaining the principle of an ordinary imaging optical system.

FIG. 15 is a schematic diagram illustrating a structure of the optical resolution improvement apparatus of this embodiment.

In this embodiment, a grating 54 similar to that in FIG. 14 is employed for another optical system. This embodiment has, as illustrated in FIG. 15, a structure similar to Embodiment 5 having the reflecting mirrors 78, 79 except having the lenses 75, 76, 77. However, in this structure, a lens 55 is disposed below the reflecting mirror 78 and the grating 54 is disposed at a focal position of the lens 55 between the lens 55 and a photo detector 57 instead of the beam splitters 72A, 72B, 73, 74, and so on being deleted.

Moreover, the lens 75 is of a large size, and part of the luminous flux transmitted through this lens 75 is incident on the lens 55 and operates similarly to that in Embodiment 9. Further, in this structure, a lens 56 is disposed below the reflecting mirror 79, and similarly to the above, a grating 54 is disposed at a focal position of the lens 56 between the lens 56 and a photo detector 58. Accordingly, the apparatus operates similarly to the above also by the lens 56, the grating 54, the photo detector 58, and so on.

Thus, the description of Embodiment 1 to Embodiment 10 has been finished. However, in above-described Embodiment 1, the irradiating means is constituted of the transmitting antennas 11, 12 which are parabola antennas of microwave, the electromagnetic wave detecting means is constituted of the receiving antennas 13, 14 which are likewise parabola antennas, the signal generating means is constituted of the signal generating device 16, and the measuring means is constituted of the measuring device 17, thereby constituting the distance measurement system using microwaves. However, the irradiating means may be a laser light source or a simple light source, the electromagnetic wave detecting means may be a photo detector capable of detecting a light, and the signal generating means and the measuring means may be devices or the like capable of processing signals from the photo detector.

Note that although the photo detector 28 is used in Embodiment 2 to Embodiment 4, it is conceivable that this photo detector 28 is omitted, the to object under measurement G1, G2 is not present or the objective lens 31 is largely defocused to perform two-dimensional scanning, and phase information is stored in the memory of the data processing unit 34 together with two-dimensional scanning information. This phase information is a phase displacement which an optical system and an electric system have, and is thus by taking this information as reference values, phase information of the case where the object under measurement G1, G2 is present can be corrected to thereby obtain true phase information. In this manner, the photo detector 28 is no longer necessary, and correction values can be obtained before observing the object under measurement G1, G2, thereby allowing measurement with high accuracy.

By obtaining correction values before observing the object under measurement G1, G2 in this manner, particularly in Embodiment 3, an enormous effect can be provided for applications such as monitoring in the case where cells or the like are flown in a micro-channel, categorizing the cells after judgment of cell shape is performed, and the like.

Specifically, since the micro-channel is an element in which cells or the like are flown in one direction, one-dimensional scanning device which scans in a direction perpendicular to the direction of the channel may be prepared instead of the two-dimensional scanning device 26 of the Embodiments 2, 3. In this manner, as the reference phase, only phases related to a very few points only in the one-dimensional scanning direction may be stored in the memory, and also the optical system becomes simple. Note that the point that similar effects can be obtained when intensity information is obtained is the same as described above, and thus is omitted.

In the foregoing, the embodiments according to the present invention have been described. However, the invention is not limited to the above-described embodiments, and various modifications can be made to implement the invention within the range not departing from the spirit of the present invention.

The distance measurement system of the present invention is not only capable of measuring the distance to an object under measurement and the shape of an object under measurement, but is applicable to measurement is apparatuses of various types, such as microscopes.

Further, the optical resolution improvement apparatus of the present invention is applicable not only to microscopes but to various types of optical apparatuses and measurement apparatuses using electromagnetic waves having wave motion, and is capable of improving the resolutions of these optical apparatuses and measurement apparatuses using electromagnetic waves having wave motion.

What is claimed is:

1. A distance measurement system, comprising:
   an irradiating means for irradiating two coherent electromagnetic waves having frequencies different from each other to an object under measurement in a partially displacing manner while having a same area;
   an electromagnetic wave detecting means for detecting electromagnetic waves from at least two or more areas on the object under measurement with a boundary line being interposed therebetween to extend in a direction substantially perpendicular to the displacement direction;
   a signal generating means for generating a difference signal or a summation signal of respective outputs of the electromagnetic waves detected in the electromagnetic wave detecting means at symmetrical positions with respect to the boundary line; and
   a measuring means for obtaining a phase difference or intensity difference of the difference signal or summation signal to obtain measurement values.

2. The distance measurement system according to claim 1, wherein the irradiating means is constituted of two transmitting antennas each transmitting a microwave, and the electromagnetic wave detecting means is constituted of at least two or more receiving antennas each receiving a microwave.

3. The distance measurement system according to claim 1, wherein a memory which stores measurement data is connected to the measuring means.

4. A distance measurement system, comprising:
   a light source emitting a coherent light;
   a first means for modulating the light emitted from the light source into two lights which have frequencies different from each other and are irradiated separately adjacent to each other;
   a second means for one-dimensionally or two-dimensionally scanning the two lights;
   a third means for irradiating an object under measurement with the two lights which are two-dimensionally scanned, the two lights being partially displaced while having a same area;
   a fourth means for receiving at least two or more divided reflected lights or transmitted lights from the object under measurement with a boundary line being interposed therebetween in a direction substantially perpendicular to the direction in which the two lights are separated;
   a fifth means for generating a difference signal or a summation signal of respective outputs of the lights received by the fourth means in areas with the boundary line being interposed therebetween; and
   a sixth means for obtaining a phase difference or an intensity difference of the difference signal or the summation signal to obtain a measurement value.

5. The distance measurement system according to claim 4, wherein the first means is constituted of an acoustic optical device or a spatial modulator, and two modulation signals are applied to the acoustic optical device or the spatial modulator.

6. The distance measurement system according to claim 4, wherein the second means is constituted of two one-dimensional scanning elements combined for two-dimensional scanning or a two-dimensional scanning element.

7. The distance measurement system according to claim 4, wherein the third means irradiates the object under measurement with parallel lights, convergent lights, or divergent lights.

8. The distance measurement system according to claim 4, wherein the sixth means uses heterodyne detection based on a difference between two modulated frequencies.

9. An optical resolution improvement apparatus, comprising:
   a light source irradiating a light, which is irradiated convergently or irradiated in parallel, to an object under measurement;

a first light processing member located on an irradiation optical axis of the convergent irradiation or the parallel irradiation and receiving and processing a luminous flux emitted from the object under measurement;

a first photo detector having at least two divided photo detectors which receive luminous fluxes of respective side portions with the irradiation, optical axis being interposed therebetween within a luminous flux which is a transmitted light emitted from the first light processing member;

a pair of second light processing members each located on a tilted optical axis having a tilt with respect to the irradiation optical axis on one of light receiving sides of the divided photo detectors of the first photo detector, and receiving and processing a luminous flux emitted from the object under measurement and making the luminous flux and a luminous flux emitted from the first light processing member interfere with each other;

a pair of second photo detectors receiving the luminous fluxes made to interfere by the pair of second light processing members; and an output difference detection unit detecting an output difference between the divided photo detectors located with the irradiation optical axis of the first photo detector being interposed therebetween and an output difference between the pair of second photo detectors.

10. The optical resolution improvement apparatus according to claim 9, wherein the light irradiated from the light source to the object under measurement is irradiated convergently, the first light processing member is constituted of a first lens converting the luminous flux emitted from the object under measurement into a parallel luminous flux, and the second light processing members are constituted of a pair of second lenses each converting the luminous flux emitted from the object under measurement into a parallel luminous flux and optical elements each making the luminous flux irradiated from the first lens and the luminous flux irradiated from one of the second lenses interfere with each other.

11. The optical resolution improvement apparatus according to claim 9, wherein the light irradiated from the light source to the object under measurement is irradiated in parallel, the first light processing member is constituted of a first beam splitter splitting the luminous flux emitted from the object under measurement, and the second light processing members are constituted of a pair of second beam splitters each making the luminous flux emitted from the object under measurement and one of the luminous fluxes split by the first beam splitter interfere with each other.

12. The optical resolution improvement apparatus according to claim 9, wherein a reflecting mirror reflecting an irradiated light from the second lenses to the optical element is disposed between the second lenses and the optical element, and the optical element includes:

a first beam splitter splitting the parallel luminous flux emitted from the first lens; and a second beam splitter combining the luminous flux reflected from the reflecting mirror and the luminous fluxes split by the first beam splitter.

13. The optical resolution improvement apparatus according to claim 9, wherein the pair of second photo detectors is constituted of a plurality of divided photo detectors and disposed at positions symmetrical to each other with respect to the irradiation optical axis.

14. An optical resolution improvement apparatus, comprising:

a light source irradiating a light, which is irradiated convergently or irradiated in parallel, to an object under measurement;

a first optical element located on a tilted optical axis having a tilt with respect to an irradiation optical axis of the convergent irradiation or the parallel irradiation and making two luminous fluxes interfere with each other;

a plurality of first photo detectors each detecting the luminous fluxes made to interfere by the first optical element;

a second optical element located on a tilted optical axis having a tilt reverse to that of the first optical element with respect to an irradiation optical axis of the convergent irradiation or the parallel irradiation and making two luminous fluxes interfere with each other;

a plurality of second photo detectors each detecting the luminous fluxes made to interfere by the second optical element; and an output difference detection unit detecting an output value of a difference between a light receiving output of one of the plurality of first photo detectors and a light receiving output of one of the plurality of second photo detectors.

15. The optical resolution improvement apparatus according to claim 14, wherein the light irradiated from the light source to the object under measurement is irradiated convergently, the apparatus comprises a lens located on the tilted optical axis having a tilt with respect to an irradiation optical axis of the convergent irradiation and converting a luminous flux emitted from the object under measurement into a parallel luminous flux, the first optical element makes a first luminous flux passing through a portion of the lens close to the irradiation optical axis of a luminous flux incident on the lens and a second luminous flux passing through one half surface of the lens which is far from the irradiation optical axis interfere with each other, and the second optical element is disposed in an opposite direction of the first optical element with respect to the tilted optical axis, and makes the first luminous flux and the second luminous flux interfere with each other.

16. The optical resolution improvement apparatus according to claim 14, wherein the light irradiated from the light source to the object under measurement is irradiated in parallel, and the first and second optical elements each have:

a first lens located on the tilted optical axis and converging a luminous flux emitted from the object under measurement;

a second lens converting a first luminous flux of one half surface of the first lens close to the irradiation optical axis of a luminous flux emitted from the first lens into a parallel luminous flux;

a third lens converting a second luminous flux of the other half surface of the first lens far from the irradiation optical axis into a parallel luminous flux; and an optical element making luminous fluxes emitted from the second lens and the third lens interfere with each other.

17. The optical resolution improvement apparatus according to claim 14, wherein the first and second optical elements include:

a first prism reversing the first luminous flux; and a second prism shifting and overlapping a luminous flux from the first prism and the second luminous flux.

18. The optical resolution improvement apparatus according to claim 14, wherein the first and second optical elements include:

a mirror reflecting the second luminous flux; and a beam splitter combining the first luminous flux and the luminous flux reflected by the mirror.

19. The optical resolution improvement apparatus according to claim 14, wherein the first and second optical elements are constituted of a convergent lens or a convergent lens and a magnifying optical system.

20. The optical resolution improvement apparatus according to claim 14, wherein the first and second optical elements are constituted of a convergent lens and a grating disposed near a focal point of the convergent lens.

* * * * *